United States Patent
Kanand et al.

[11] Patent Number: 5,892,125
[45] Date of Patent: Apr. 6, 1999

[54] PREPARATION OF N-BUTYRALDEHYDE AND/OR N-BUTANOL

[75] Inventors: Jürgen Kanand, Bad Dürkheim; Michael Röper, Wachenheim; Rocco Paciello, Bad Dürkheim; Alfred Thome, Speyer, all of Germany

[73] Assignee: BASF Aktiengesellschaft, Ludwigshafen, Germany

[21] Appl. No.: 793,480

[22] PCT Filed: Aug. 24, 1995

[86] PCT No.: PCT/EP95/03358

§ 371 Date: Jul. 23, 1997

§ 102(e) Date: Jul. 23, 1997

[87] PCT Pub. No.: WO96/07630

PCT Pub. Date: Mar. 14, 1996

[30] Foreign Application Priority Data

Sep. 3, 1994 [DE] Germany .......... 44 31 528.7

[51] Int. Cl.$^6$ .................. C07C 47/02
[52] U.S. Cl. .......... 568/449; 568/450; 568/904
[58] Field of Search .............. 568/449, 450, 568/487, 904

[56] References Cited

U.S. PATENT DOCUMENTS

| | | | |
|---|---|---|---|
| 3,391,192 | 7/1968 | Zuech .................. 260/601 |
| 3,449,445 | 6/1969 | Wetherill . | |
| 3,714,270 | 1/1973 | Fenton . | |
| 3,725,493 | 4/1973 | Brennan . | |
| 4,120,901 | 10/1978 | Hobbs et al. . | |
| 4,204,997 | 5/1980 | Hobbs et al. . | |
| 4,310,440 | 1/1982 | Wilson et al. . | |
| 4,318,845 | 3/1982 | Spivack et al. . | |
| 4,362,830 | 12/1982 | Minagawa et al. . | |
| 4,440,871 | 4/1984 | Lok et al. . | |
| 4,500,651 | 2/1985 | Lok et al. . | |
| 4,554,143 | 11/1985 | Messina et al. . | |
| 4,567,029 | 1/1986 | Wilson et al. . | |
| 4,675,307 | 6/1987 | Taniguchi et al. . | |
| 4,861,890 | 8/1989 | Heiser et al. . | |
| 4,891,458 | 1/1990 | Innes et al. . | |
| 5,204,997 | 4/1993 | Hobbs et al. . | |
| 5,227,544 | 7/1993 | Thurman .................. 568/881 |

FOREIGN PATENT DOCUMENTS

| | | |
|---|---|---|
| 2 261 | 6/1979 | European Pat. Off. . |
| 2 821 | 7/1979 | European Pat. Off. . |
| 9 115 | 4/1980 | European Pat. Off. . |
| 44 444 | 1/1982 | European Pat. Off. . |
| 68 506 | 1/1983 | European Pat. Off. . |
| 71 281 | 2/1983 | European Pat. Off. . |
| 100 406 | 2/1984 | European Pat. Off. . |
| 146 218 | 7/1985 | European Pat. Off. . |
| 155 505 | 9/1985 | European Pat. Off. . |
| 158 349 | 10/1985 | European Pat. Off. . |
| 158 976 | 10/1985 | European Pat. Off. . |
| 176 398 | 4/1986 | European Pat. Off. . |
| 213 639 | 3/1987 | European Pat. Off. . |
| 214 622 | 3/1987 | European Pat. Off. . |
| 257 411 | 3/1988 | European Pat. Off. . |
| 279 081 | 8/1988 | European Pat. Off. . |
| 285 420 | 10/1988 | European Pat. Off. . |
| 311 619 | 4/1989 | European Pat. Off. . |
| 353 770 | 2/1990 | European Pat. Off. . |
| 398 132 | 11/1990 | European Pat. Off. . |
| 415 202 | 3/1991 | European Pat. Off. . |
| 472 071 | 2/1992 | European Pat. Off. . |
| 2 321 101 | 11/1974 | Germany . |
| 25 10 817 | 11/1976 | Germany . |

(List continued on next page.)

OTHER PUBLICATIONS

Journal of Organic Chemistry, 37, pp. 4243–4245 —Schlott et al, 1972.

(List continued on next page.)

*Primary Examiner*—Gary Geist
*Assistant Examiner*—Sreeni Padmanabhan
*Attorney, Agent, or Firm*—Keil & Weinkauf

[57] ABSTRACT

A process for the preparation of n-butyraldehyde and/or n-butanol, in which a) 1,3-butadiene is caused to react with an amine of the formula I $$R^1R^2NH, \quad I$$

in which $R^1$ and $R^2$ independently denote hydrogen, optionally substituted aliphatic or cycloaliphatic radicals, or aryl or aralkyl radicals or are linked to form a bridging member which can contain hetero atoms, at elevated temperature and under superatmospheric pressure in the presence of a compound of a Group VIIIb element and in the presence of an alkali metal amide or a basic metal oxide to form a mixture of the adducts of the formulas II

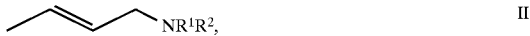

and III

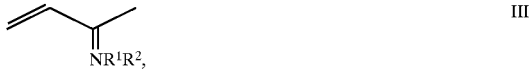

b) the adduct III is isomerized to the adduct II, c) the adduct II is isomerized in the presence of a homogeneous or heterogeneous transition metal element catalyst in the liquid phase or in the presence of a heterogeneous catalyst containing a transition metal element in the gaseous phase to form the enamine of the formula IV

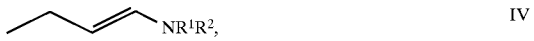

and d) n-butyraldehyde and/or n-butanol is/are produced from this enamine.

8 Claims, No Drawings

FOREIGN PATENT DOCUMENTS

| | | |
|---|---|---|
| 27 33 796 | 2/1978 | Germany . |
| 23 66 264 | 4/1980 | Germany . |
| 39 02 357 | 8/1990 | Germany . |
| 39 04 083 | 8/1990 | Germany . |
| 39 32 332 | 4/1991 | Germany . |
| 44 00 837 | 7/1995 | Germany . |
| WO 90/06810 | 6/1990 | WIPO . |

OTHER PUBLICATIONS

Journal of Catalysis, 85, 509–518 —Kakuns et al, 1984.

Journal of the Chemical Society–Peakin II 1511–1517—Baker et al, 1974.

Journal of the American Chemical Society, 106 5208–5217—Tain et al, 1984.

Journal of Organometallic Chem. vol. 382, 1990, Herrmann.

Chem. Letters, pp. 1987–1988, The Chem. Soc. of Japan, 1982 Takabe et al.

Angew. Chem. 103 (1991) Nr. 2, Herrmann, 183–185.

Angew. Chem. 100 (1988) 1269–1286, Herrmann, 1269–1285.

Angew. Chem. 100 (1988), Nr. 3, Herrmann, 420–421.

Journal of Organometallic Chem., 297 (1985), Herrmann, C5–C7.

Journal of Organic Chemistry, vol. 37, Nov.–Dec. 1972 Schlott et al., Lithium Amide Catalyzed . . . .

Polymer–Supported Reactions in Organic Synthesis, 1980, Charles U. Pittman, Jr., 249–291.

Reactive Polymers, 9 (1988) 249–255, Zhuangyu et al. (Poly(Styryl) Phenanthroline) Palladium . . . .

Derivatives of 1,10–Phenanthroline . . . , Dickeson et al., Aust. J. Chem., 1970, 23, 1023–7.

Synthesis, The Specific Synthesis of Pyridines . . . , 1–24, Angew. Chem. 65, 473 (1953).

Jrl. Am. Chem Soc, vol. 107, 1985, Jan.–Feb., 428–432, Doering et al.

Journal of Organometallic Chem., vol. 251, 1983, Tatsumi et al. Reactions of Allylic Compounds Such as Allyl . . . 105–112.

Journal of the Am. Chem. Soc., vol. 100, 1978, 3949–3950.

JP–A 79/5907—J. Am. Chem. Soc. 100, 3949, (1978).

Axially Dissymmetric Diphosphines . . . , Helvetica Chimica Acta vol. 74 (1991) 370–389.

Helvetica Chimica Acta, vol. 73, 1990, Schmid et al. 1258–1275.

Highly Enantioselective Isomerization of . . . , J. Am. CHem. Soc. vol. 106, 1984, 5208–5217, Tani et al.

Tetrahedron Lett. No. 29, p. 2531, 1976, Pergamon Press.

Tetrahaedron Lett. No. 25, pp. 2863–2866, 1966, Pergamon Press.

Tetrahedron Lett. No. 2, pp. 69–73, 1962, Pergamon Press.

Base–catalysed Prototropic Isomerization . . . J. Chem. Soc., (C), 1968 2048–2050.

Double–Bond Migration of Allylamine . . . , Jour. of Catalysis 65, 245–252 (1980).

Angew. Chem. vol. 102, 1990, 408–414.

Reaction of Amines with 1,3–Dienes . . . , Journal of the Chem. Soc. 1974, 1511–1517.

Tetrahedron Letts. No. 27, pp. 2773–2776, 1972 Pergamon press.

Palladium–Catalyzed Additions of Amines to COnjugated Dienes: . . . Armbruster et al. 1986, Am. Chem. Soc. 234–237.

Bull. of the Chem. Soc. of Japan, vol. 45, 1183–1191, 1972 Palladium–catalyzed Reactions of 1,3–Dienes . . . .

Chem. Abst. JA 7225321, Oct. 27, 1969.

Chem. Abst. JA 7119926, Jul. 22, 1968.

Chem. Abst., JA 7119925, Jul. 22, 1968.

Studies on Hydroaminations of Unsaturated Compounds, Vo. 38, 1981 Watanabe et al. 111–121.

Journal of Catalysis, vol. 85, 1984, Addition of Amines . . . Kakuno et al.

Unusual Selectivities in Hydroformylation . . . Journal of Am. Chem. Soc., 98:17, Aug. 18, 1976, 5402–5405.

PREPARATION OF N-BUTYRALDEHYDE AND/OR N-BUTANOL

This is the U.S. National stage application of PCT/EP95/03358 filed Aug. 24, 1995 now WO96/07630 published Mar. 14, 1996.

The present invention relates to a novel process for the preparation of n-butyraldehyde and/or n-butanol and to the use of the n-butyraidehyde synthesized by the process of the invention for the preparation of 2-ethylhexanol. The invention also relates to a process for the preparation of 2-ethylhexanol from n-butyraldehyde.

n-Butyraldehyde and n-butanol are products which are produced on a large scale in the chemical industry and have varied uses. n-Butyraldehyde is produced world-wide in amounts of more than 4 million t/yr and serves inter alia as starting material for the preparation of plasticizer alcohols. n-Butanol is employed on a large scale as solvent, for example for coating compositions.

n-Butyraldehyde is prepared nowadays on an industrial scale virtually exclusively by the hydroformylation of propene, for which purpose various processes are used, which essentially make use of cobalt or rhodium hydroformylation catalysts, (Kirk-Othmer: Encyclopedia of Chemical Technology, 4th Edition, Vol. 4, pp. 741–746, John Wiley & Sons, New York 1992).

n-Butanol is one of the quantitatively most important derivatives of n-butyraldehyde and is obtained therefrom by hydrogenation. Other processes for the preparation of n-butanol, such as the hydrogenation of crotonaldehyde, which is in turn produced by aldol condensation of acetaldehyde, are nowadays merely of historical interest or have only regional significance, such as in the case of the microbiological production of n-butanol by fermention of molasses, (Kirk-Othmer: Encyclopedia of Chemical Technology, 4th Edition, Vol. 4, pp. 694–696: John Wiley Sons, New York 1992). These processes, particularly the hydroformylation of propene, demand high investments, for example, for the construction of high-pressure plant for the cobalt-catalyzed hydroformylation or for the purchase of the expensive rhodium catalyst, the plant required for handling during hydroformylation and for working up the spent rhodium-containing catalyst solution. Furthermore the preparation of n-butyraldehyde by the hydroformylation process requires the presence of a synthesis gas plant for the preparation of the synthesis gas required for the hydroformylation. A further drawback of the process is the unavoidable formation of large quantities of the by-product isobutyraldehyde, which, on account of its restricted possibility of further usage in quantity, has a low economical rating.

1,3-Butadiene is a basic chemical which is produced in large amounts in steam crackers and is isolated, by extraction, from the $C_4$ cut obtained in the cracker, for example, by means of N-methyl pyrrolidone. Although 1,3-butadiene is available in large amounts and is a very cheap raw material, no industrially usable process has been developed hitherto for the preparation of n-butyraldehyde or n-butanol on the basis of 1,3-butadiene. One reason for this is the tendency of 1,3-butadiene to undergo dimerization and polymerization reactions and the formation of mixtures of 1,2- and 1,4-adducts in addition reactions. The reason for this chemical behavior is the presence of two conjugated double bonds in the 1,3-butadiene molecule (Kirk-Othmer: Encyclopedia of Chemical Technology, 4th Edition, Vol. 4, pp. 676–683, John Wiley & Sons, New York 1992).

U.S. Pat. No. 3,391,192 discloses that amines react with 1,3-butadiene in the presence of alkali metal amides to form the corresponding allyl amines. Falk at al (*J. Org. Chem.* 37, 4243 (1972)) investigated the lithium amide-catalyzed additon of amines to butadiene in relation to the solvent and the amine. Kanuno and Hattori (*J. Catal.* 85 (1984) 509) describe the catalyzed reaction of butadiene with amines using solid base catalysts such as MgO or CaO. In their experiments, the reaction mixture is passed through a circulated gas reactor over a fixed bed under a total pressure of 100 torr. According to U.S. Pat. No. 4,675,307, strongly basic hydrotalcites are suitable for use as catalysts for the hydroamination.

Transition metal complexes have also been used as catalysts for the addition of amines to 1,3-butadiene. Watanabe et al (*Kenkyu Kokoku-Asali Garasu Kogyo Gijiutsu Shoreikai* 38, 111 (1981)) describe the reaction of various primary and secondary amines with butadiene in the presence of palladium and platinum complexes. Secondary amines mainly yield butenyl amines, depending on the type of catalyst used, whereas primary amines produce mixtures of 1:1 adducts with 1:2 adducts and 1:4 adducts. JP-A 71/19,925, JP-A 71/19,926, and JP-A 72/25,321 relate to the catalyzed synthesis of alkenyl amines using palladium compounds and chelating phosphine ligands. Takahashi et al (*Bull. Chem. Soc. Jap.* 45, 1183 (1972)) carry out this reaction in the presence of, in addition, sodium phenolate/phenol. Another known co-catalyst for palladium-catalyzed hydroamination is triethylammonium iodide (Arbruster et al, *Organomet.* 5, 234 (1986)), which is used to increase the selectivity of the reaction toward the monoadduct. U.S. Pat. No. 4,120,901 discloses that the addition of ammonia to produce 1-aminobutene-2 is successfully carried out using palladium complexes in primary or secondary alcohols acting as solvent. The amination of 1,3-dienes in the presence of optically active phosphorus compounds is described in U.S. Pat. No. 4,204,997.

Ligand effects of the rhodium-catalyzed reaction of butadiene with amines has been investigated by Baker and Halliday (*Tetrahedron Lett.* 2773 (1972)). EP-A 176,398 reveals the successful reaction of secondary amines with 1,3-butadiene in the presence of water-soluble rhodium complexes. Co-catalysts used in this case are trisulfonated phosphines. Herrmann et al (*Angew. Chem.* 102, 408 (1990)) make use of appropriate water-soluble platinum complexes for the reaction of isoprene with dimethylamine.

In addition to the said transition metals, it is known to use compounds of nickel, cobalt, or iridium for such hydroaminations. Thus Baker et al (*J. Chem. Soc. Perkin II,* 1511 (1 974)) have investigated the reaction of butadiene in the presence of catalytic amounts of nickel acetylacetonate and phosphite ligands. The same reaction, carried out using cobalt or iridium catalysts, produces mixtures of 1:2 adducts with 1:1 adductsFor the isomerization of allyl ethers to anamines a series of reagents has already been examined.

The isomerization of 1-N-pyrrolidino-2-prepene using basic heterogeneous oxide catalysts such as MgO, CaO, or BaO is described by Hattori et al (*J. Catal.* 65, 245 (1980)). Hubert (*J. Chem. Soc.* (C), 2048 (1968)) effects the rearrangement of allyamines in the presence of patassium amide supported on aluminum oxide.

Apart from the said heterogeneous catalysts, use has been made of homogeneous catalysts for the isomerization of allylamines in the liquid phase.

Strong bases soluble in the organic medium, such as potassium tert-butanolate, have been investigated by Price et al (*Tetrahedron Lett.* 2863 (1 966)) and Martinez (*Tetrahedron* 34, 3027 (1978)) for the conversion of allylamines to enamines.

Not only such base-catalyzed reactions but also reactions involving the use of transition metal compounds are described.

Isomerizations of secondary and tertiary allylamines using rhodium/diphosphine complexes to produce enamines or imines are described by Otsuka et al (*J. Am. Chem. Soc.* 106, 5208 (1984)) and by Schmid et al (*Helv. Chim. Acta.* 73, 1258 (1990)); *Helv. Chim. Acta* 74, 370 (1991)). U.S. Pat. No. 4,861,890, EP-A 0,068,506, EP-A 257,411, and Otsuka (*Org. Synth.* 67, 33 (1989)) disclose that β,γ-unsaturated amines isomerize to enamines in the presence of rhodium/diphosphine complexes, which enamines are converted to their corresponding aldehydes on hydrolysis. JP-A 79/5907 and Otsuka (*J. Am. Chem. Soc.* 100, 3949 (1978)) teach the cobalt/phosphine complex-catalyzed rearrangement of allylamines.

In addition to said compounds, use can be made of molybdenum compounds (Tatsumi et al, *J. Organomet. Chem.* 252, 105 (1983)) or ruthenium compounds (EP-A 398,132; Doering et al, *J. Am. Chem. Soc.* 107, 428 (1985)).

The direct single-stage conversion of allylamines to the corresponding aldehydes or alcohols is not known.

It was thus the object of the present invention to provide an economical process which can be employed on an industrial scale for the preparation of n-butyraldehyde and/or n-butanol, which makes it possible to prepare these products at high yield and selectivity. In particular, the amount of by-product formed in the process should be low or the said by-products should themselves be sought-after commercial products. Furthermore the process should be flexible so as to make it possible to prepare n-butyraldehyde and/or n-butanol as required, in accordance with the demand for these compounds. The process should not demand the presence of a synthesis gas plant or necessitate the use of high pressure facilities.

2-Ethylhexanol is manufactured on an industrial scale via the aldol reaction of n-butyraldehyde followed by hydrogenation of the aldol product (Kirk-Othmer, *Encyclopedia of Chemical Technology* 4th Edition, 1991, Vol. 1, p 893; *Ullmanns Encyklopädie der techn. Chemie,* 4th Edition, 1974, Vol. 4, p 214). The alcohol is used in the synthesis of the plasticizer bis(2-ethylhexyl)phthalate.

Thus another object of the invention is to provide a process by means of which n-butyraldehyde can be converted to 2-ethylhexanol without intermediate, energy-consuming purification.

Accordingly, we have found a process for the preparation of n-butyraldehyde and/or n-butanol, wherein a) 1,3-butadiene is caused to react with an amine of the formula I $$R^1R^2NH, \qquad I$$

in which $R^1$ and $R^2$ independently denote hydrogen, optionally substituted aliphatic or cycloaliphatic radicals, or aryl or aralkyl radicals or are linked to form a bridging member which can contain hetero atoms, at elevated temperature and under superatmospheric pressure in the presence of a compound of a Group VIIIb element and in the presence of an alkali metal amide or a basic metal oxide to form a mixture of the adducts of the formulas II

$NR^1R^2,$  II and III

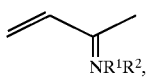
$NR^1R^2,$  III b) the adduct III is isomerized to the adduct II, c) the adduct II is isomerized in the presence of a homogeneous or heterogeneous transition metal element catalyst in the liquid phase or in the presence of a heterogeneous catalyst containing a transition metal element in the gaseous phase to form the enamine of the formula IV

$NR^1R^2,$  IV and d) n-butyraldehyde and/or n-butanol is/are produced from this enamine IV by the reaction thereof with hydrogen and water or water only in the presence of a homogeneous or heterogeneous transition metal element catalyst in the liquid phase or in the presence of a heterogeneous transition metal element catalyst in the gaseous phase and in the presence of an acid or in the presence of one of said catalysts and an acid, and the amine I is again liberated, and the liberated amine I is recycled to the stage defined above as partial reaction a).

We have also found a method of using the n-butyraldehyde synthesized by the process of the invention for the preparation of 2-ethylhexanol, and a process for the preparation of 2-ethylhexanol.

The process of the invention for the preparation of n-butyraldehyde and/or n-butanol is thus composed of four partial reactions a) to d). The reactions c) and d) can be carried out individually, successively, in at least 2 process stages or virtually simultaneously in a single process stage, as required. The same applies to the reactions a) and b), in which case the isomerization of the adduct III to the adduct II in accordance with partial reaction b) takes place following recycling of the adduct III to the process stage involving the addition of the amine $R^1R^2NH$ to 1,3-butadiene concurrently with the addition reaction defined as partial reaction a). By this means it is a simple matter to adjust the process perameters for the process of the invention to the local conditions at the site where a plant for carrying out the process is installed, for example by integrating plant units already present at the site in the system required for the process of the invention.

The term "process stage" is used in this application for a plant unit, in which any one of the reactions a) to d) takes place over the catalyst(s) employed in this plant unit or in which a number, particularly two, of these reactions, occur in parallel over the catalyst(s) used in this plant unit. The hydrolysis or the combined hydrolysis/hydrogenation of the enamine IV defined as partial reaction d) is, unless otherwise stated in this application, considered to be an individual reaction.

If the catalyst used in a plant unit or if each of the catalysts used in a plant unit is capable of catalyzing, under the reaction conditions used therein, for example, the isomerization of the adduct II to the enamine IV defined as partial reaction c) and the hydrolysis or hydrogenation of the enamine IV to n-butyraldehyde and/or n-butanol defined as partial reaction d), so that no strict spatial separation of these reactions in the unit can be ascertained, this application speaks of the execution of the reactions c) and d) as being in a 'single process stage'. A unit can include both a single reactor and a number of in-line reactors, which are filled with the same or, optionally, different catalysts and are operated in the same mode of operation and under the same or different temperature and pressure conditions. By 'mode of operation' we mean operating either in the liquid phase using a homogeneous catalyst or operating in the liquid phase using a heterogeneous catalyst or operating in the gaseous phase. It follows then that this application will not speak of, for example, a 'reaction in a single process stage', if in the individual successive reactors catalysts are used, which are capable only of catalyzing one specific reaction or if these reactors are operated with different operational modi.

The process of the invention is described in greater detail below:

In the process stage a) 1,3-butadiene is caused to react with the amine $R^1R^2NH$ I in the presence of a catalyst according to equation (1)

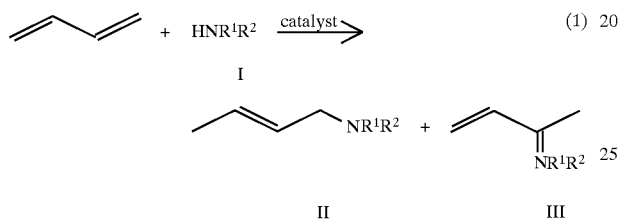

to form the mono-adducts of formulas II and III and, when use is made of a primary amine or ammonia, to further form mixtures of di-adducts and tri-adducts and also to form telomers. In the resulting mono-adduct II the double bond can be present in both the cis and trans forms, but this bears no relevance on the further course of the process. The adducts II and III are formed, depending on the reaction conditions and catalyst used, generally in a molar ratio of from 1:1 to 20:1.

The nature of the amine $R^1R^2NH$ I employed in the reaction is not usually crucial for the process. Ammonia and both primary and secondary amines can be used. The amines can carry a number of different radicals $R^1$ and $R^2$. Suitable radicals are, therefore, aliphatic radicals such as alkyl radicals, in particular $C_1$–$C_{20}$ alkyl radicals, and $C_2$–$C_{20}$ alkenyl radicals, and also cycloalkyl radicals, in particular $C_4$–$C_{10}$ cycloalkyl radicals, and $C_4$–$C_{10}$ cycloalkenyl radicals. The non-cyclic radicals may be linear or branched. The aliphatic radicals can carry substituents which are inert under the conditions of the reaction, preferably one or two such substituents, examples of which are $C_1$–$C_{10}$ alkoxy groups, amino groups, and hydroxy groups. The radicals $R^1$ and $R^2$ may also independently stand for aryl groups, preferably $C_6$–$C_{10}$ aryl such as phenyl, which aryl groups may be substituted by inert radicals such as $C_1$–$C_4$ alkyl. Aralkyl radicals, preferably $C_7$–$C_{11}$ aralkyl, are also suitable as substituents on the amine I.

The radicals $R^1$ and $R^2$ may also be linked to form a bridging member so as to form a nitrogen-containing ring. The number of bridging atoms is preferably from 3 to 6. The bridging member can contain hetero atoms such as oxygen or nitrogen. It may be saturated or unsaturated or be part of an aromatic ring. In addition, it can carry inert substituents such as $C_1$–$C_4$ alkyl groups.

Ammonia, $C_1$–$C_6$ N-alkylanilines, and amines are particularly preferred, in which the radicals $R^1$ and $R^2$ independently stand for branched-chain or straight-chain $C_1$–$C_6$ alkyl radicals, $C_2$–$C_6$ alkenyl radicals, or $C_4$–$C_7$ cycloalkyl radicals.

The following is a list of amines which can be used in the present invention, given by way of example only:

Methylamine, ethylamine, n-propylamine, isopropylamine, n-butylamine, isobutylamine, sec-butylamine, tert-butylamine, isopentylamine, 3-methyl-2-butylamine, n-hexylamine, octylamine, 2-ethylhexylamine, decylamine, tert-hexylamine, 1,1,3,3-tetramethylbutylamine, allylamine, 2-butenylamine, 3-pentenylamine, hexylamine, n-heptylamine, cyclopentylamine, cyclohexylamine, methylcyclohexylamine, cyclooctylamine, cyclodecylamine, benzylamine, 2-phenylethylamine, 4-methoxyphenylethylamine, aniline, toluidine, 2-diethylaminoethylamine, dimethylaminopropylamine, 2-aminoethanol, 1-amino-2-propanol, 3-aminopropanol-1, 2-aminobutanol-1, dimethylamine, diethylamine, di-n-propylamine, diisopropylamine, di-n-butylamine, diisobutylamine, di-sec-butylamine, di-n-pentylamine, diisopentylamine, di-n-hexyl-amine, di-2-ethylhexylamine, n-methylbutylamine, n-ethylbutylamine, di-2-methoxyethylamine, n-methylcyclohexylamine, n-ethylcyclohexylamine, n-methylethylamine, dicyclohexylamine, n-ethylaniline, diamylamine, di-n-octylamine, allylmethylamine, 2-butenylethylamine, dialkylamine, n-methylbenzylamine, allylmethallylamine, pyrrolidine, piperidine, 4-methylpiperidine, morpholine, 2,6-dimethylmorpholine, imidazol, 2-methylimidazol, 4-methylimidazol, piperazine, 1-ethylpiperazine, pyrazol, ethylenediamine, 1,3-diaminopropane, 1,2-propyidiamine, neopentandiamine, hexamethylenediamine, diethylenetriamine A large number of transition metal element catalysts can be used in process stage a), for example, compounds of palladium, platinum, nickel, rhodium, cobalt, or iridium, or strongly basic compounds such as metal amides, metal alcoholates, and hydrotalcites.

In one embodiment of the process of the invention the addition of the amine I can be effected by means of a catalyst homogeneously dissolved in the reaction medium or a heterogenized transition metal element catalyst, which catalyst contains a Group VIIIb element such as palladium, platinum, nickel, rhodium, rhenium, cobalt, or iridium, preferably palladium or nickel.

Advantageously, these transition metal element catalysts, particularly the palladium and nickel catalysts, are used in the form of their complexes with, e.g., phosphine ligands, 2,2'-bipyridine ligands, or 1,10-phenanthroline lagands, such complexes being homogeneously soluble in the reaction medium. In the process of the invention a large number of different phosphine ligands, 2,2'-bipyridine ligands, or 1,10-phenanthroline lagands can be used for the purpose of complexing the Group VIIIb metals, particularly palladium and nickel. Suitable ligands are both monodentate and polydentate, particularly bidentate, phosphine ligands. Suitable ligands are, e.g., trialkyl phosphines, triaryl phosphines, alkyldiaryl phosphines, aryidialkyl phosphines, aryl diphosphines, alkyl diphosphines, and arylalkyl diphosphines. The alkyl group-carrying ligands may contain the same or different $C_1$–$C_{10}$, preferably $C_1$–$C_6$, alkyl or cycloalkyl groups. The aryl group-carrying ligands can contain the same or different $C_6$–$C_{12}$ aryl groups, particularly the phenyl or naphthyl group, or alternatively diphenyl groups. Furthermore ligands for complexing the Group VIIIb elements can be used which carry heterocycloaliphatic groups such as pyrrolidine, imidazolidine, piperidine, morpholine, oxazolidine, piperazine, or triazolidine groups or heteroaromatic groups such as pyrrole, imidazole, oxazole, indole, pyridine, quinoline, pyrimidine, pyrazole, pyrazine, pyridazine, or quinoxaline groups together with other alkyl or aryl groups. The alkyl or aryl groups of the ligands can be unsubstituted or carry substituents which are inert under the reaction conditions, such as $C_1$–$C_6$ alkyl, nitro, cyano or sulfonate groups.

Theoretically there is no limit to the usability of such ligands for complexing the Group VIIIb elements, particularly palladium and nickel, in the process of the invention. However for reasons of cost it is preferred to use ligands which can be prepared in a simple manner. A list of such ligands is given below merely by way of example:

trimethylphosphine, triethylphosphine, tripropylphosphine, triisopropylphosphine, tributylphosphine, trioctylphosphine, tridecylphosphine, tricyclopentylphosphine, tricyclohexylphosphine, triphenylphosphine, tritolylphosphine, cyclohexyldiphenylphosphine, tetraphenyldiphosphinomethane, 1,2-bis(diphenylphosphino)ethane, tetramethyidiphosphinomethane, tetraethyldiphosphinomethane, 1,3-bis(diphenylphosphino)propane, 1,4-bis(diphenylphosphino)butane, bis(di-tert-butyldiphosphino)methane, 1,2-bis(dimethylphosphino)ethane, 1,2-bis(diethylphosphine)ethane, 1,2-bis(dipropylphosphino)ethane, 1,2-bis(diisopropylphosphino)ethane, 1,2-bis(dibutylphosphino)ethane, 1,2-bis(di-tert-butylphosphino)ethane, 1,2-bis(dicyclohexylphosphino)ethane, the salts of triphenylphosphine trisulfonate or of triphenylphosphine monosulfonate, as well as the bisphosphine ligands described in EP-A 279,018, EP-A 311,619, WO 90/06810 and EP-A 71,281. Apart from using the processes described in the aforementioned patent applications, the alkyl or aryl phosphine ligands can be prepared by conventional methods as described, for example, in Houben-Weyl, *Methoden der Organischen Chemie,* Vol. XII/1, 4th Edition, pp. 17–65 and pp. 182–186, Thieme, Stuttgart, 1963 and Vol. E 1, 4th Edition, pp. 106–199, Thieme, Stuttgart, 1982.

In addition to phosphine ligands use can be made in the process of the invention, to advantage, of 2,2'-bipyridine or 1,10-phenanthroline ligands of alkyl- or aryl-substituted or anellated 2,2'-bipyridine or 1,10-phenanthroline derivatives, which contain the (—N═C—C═N—) grouping responsible for the complexing property of the 2,2'-bipyridine or 1,10-phenanthroline ligands, for example, 2,2'-biquinoline, 4,7-diphenyl-1,10-phenanthroline, 4,5-diazafluorene, dipyrido[3,2a:2',3'-c]phenazine, 2,2',6',2"-terpyridine and the like. Some of these ligands are commercially available, e.g., 2,2'-bipyridine or 1,10-phenanthroline, or can be prepared by the methods described in *Synthesis* 1, (1976) or *Aust. J. Chem.* 23, 1023 (1970).

The complexes of Group VIIIb elements, particularly of palladium and nickel, which can be used in the process of the invention for the partial reaction a) can be produced in situ in the reaction mixture or be preformed and added to the reaction mixture. For the formation in situ of these complexes it is general to operate in such a manner that compounds of the Group VIIIb elements, e.g., their halides, preferably their chlorides, bromides, or iodides, the nitrates, cyanides or sulfates, or complex compounds of these metals, such as acetylacetonates, carboxylates, carbonyl complexes or olefin complexes, such as ethers or butadiene complexes, are fed in to the reaction mixture together with the respective ligands, after which the complexes that can be used in the invention in partial reaction a) are formed in the reaction mixture. In this method the complexing agent is generally added in a molar ratio with respect to the Group VIIIb element of from 2:1 to 200:1, preferably from 2:1 to 10:1, and more preferably from 2:1 to 4:1.

Generally, when effecting the addition of the amine $R^1R^2NH$ to 1,3-butadiene in process stage a) of the process of the invention, when use is made of the said Group VIIIb element komplex catalysts, particularly the palladium complex catalysts, a molar ratio of 1,3-butadiene to Group VIIIb element of from 100:1 to 100,000:1, preferably of from 200:1 to 10,000:1 and more preferably of from 400:1 to 5000:1 is used, and when the process is carried out continuously this molar ratio is based on the steady 1,3-butadiene concentration in the liquid reaction mixture.

The molar ratio of amine $R^1R^2NH$ to 1,3-butadiene can, in this embodiment of the process, be chosen within wide limits and is usually not critical. For example, the amine to be added to 1,3-butadiene can function not only as a reagent but also as a solvent for the complex catalyst. Generally therefore the process of the invention uses in the partial reaction a) a molar ratio of amine to 1,3-butadiene of from 0.5:1 to 10:1, preferably from 1:1 to 5:1 and more preferably from 1:1 to 5:1, whilst in the case of the continuous embodiment of the process these figures relate to the steady 1,3-concentration in the liquid reaction mixture.

The addition of the amine $R^1R^2NH$ to 1,3-butadiene defined as partial reaction a) of the process of the invention with the aid of the complex catalysts mentioned above is preferably carried out in the liquid phase. Generally the catalyst is dissolved in the liquid reaction medium used as initial substance and 1,3-butadiene is introduced into the reaction mixture in liquid or gaseous form, together with the alcohol. The reaction medium used can be the amine to be added to 1,3-butadiene or a solvent that is inert under the reaction conditions, preferably a high-boiling solvent. Examples of suitable solvents are condensation products which are formed during the reaction, such as amino octadienes, alkoxy dodecatrienes, and also ethers, such as dibutyl ether, diethylene glycol dibutyl ether, low molecular weight poly(ethylene glycol ether)s as well as alcohols, such as methanol or butanol.

When the process is carried out batchwise, the reaction is generally carried out in a stirred autoclave. The adducts of formulas II and III formed during this process are then advantageously separated from the reaction mixture by distillation, whilst the homogeneous catalyst containing the Group VIIIb element, particularly palladium or nickel, remains at the bottom of the distillation column, dissolved in the high-boiling solvent. The catalyst solution thus remaining at the base of the distilling apparatus can be re-used for further reactions.

When the process is carried out continuously, the 1,3-butadiene is introduced, preferably in liquid form under pressure, into the reaction mixture containing the amine $R^1R^2NH$ and the homogeneously dissolved transition metal element catalyst as well as any high-boiling solvent. The reaction is advantageously carried out in a tubular reactor or loop reactor or, preferably, in a cascade of reactors. Unconverted 1,3-butadiene is advantageously recycled during this process. The amine is advantageously continuously metered into the reaction mixture at the rate at which it is consumed in the reaction, such that it is always present in stoichiometric excess.

In another continuous embodiment of the process of the invention the 1,3-butadiene can be passed in the gaseous state through the liquid reaction medium containing the catalyst, whilst unconverted 1,3-butadiene is used to strip the relatively readily volatile adducts of the formulas II and III which are formed with the amine during the reaction, from the reaction mixture. The amine I can be continuously added to the reaction mixture during this process, at a rate corresponding to its rate of consumption during the reaction.

The addition of the amine $R^1R^2NH$ to 1,3-butadiene in the presence of the said complexes of the Group VIIIb elements, particularly palladium or nickel, is generally carried out at a temperatur of from 20° to 180° C., preferably from 50° to 150° C. and more preferably from 80° to 120° C. and under a pressure preferably of from 6 to 50 bar and more preferably under autogenous pressure.

In the process of the invention it is advantageous for the addition of the amine $R^1R^2NH$ to 1,3-butadiene in partial reaction a) to use heterogenized complex catalysts, preferably those in which the Group VIIIb element, particularly palladium or nickel, is attached to polymeric matrices. Such polymeric matrices can be resins, such as styrene-divinylbenzene resins or phenol-formaldehyde resins, to which the respective chelate ligands, i.e. phosphines, 1,10-phenanthrolines or 2,2'-bipyridines, are attached, which on the other hand form complexes with the Group VIIIb elements, particularly palladium or nickel, and thus quasi immobilize them. Suitable heterogeneous matrices for the immobilization of the Group VIIIb element complexes, particularly the palladium and nickel complexes, are inorganic support materials, following previous hydrophobization and chemical modification of their surface by means of organic reagents. Such heterogenized, polymerically attached Group VIIIb element complexes, particularly palladium and nickel complexes, can be obtained, for example, by the process described in Zhuangyu et al (*Reactive Polymers* 9, 249 (1988)). Immobilized complexes of the Group VIIIb elements can be obtained e.g., by the processes described in Hartley, *Adv. Organomet. Chem.* 15, 189 (1977), F. R. Hartley "Supported Metal Complexes", Riedel, Dordrecht 1985, K. Smith, "Solid Supports and Catalysis in Organic Synthesis", Ellis Horwood, Prentice Hall, N.Y. 1992; C. H. Pittman "Polymer supported Reactions in Organic Synthesis", p. 249, Wiley, Chichester 1980 and C. H. Pittmann, *Am. Chem. Soc.* 98, 5407 (1976) as well as *Am. N.Y. Acad. Sci.* 245, 15 (1977). The advantage of the use of such heterogenized catalysts lies particularly in the greater ease of separation of the catalyst from the reaction products and the more gentle separation achieved. This catalyst can be in the form of a fixed bed through which the reaction mixture flows or it can alternatively be suspended in the reaction mixture and mechanically separated therefrom on completion of the reaction.

In another embodiment of the process stage a) the reaction between 1,3-butadiene and the amine $R^1R^2NH$ I can be carried out in the presence of an alkali metal amide. Those amides which correspond to the amines $R^1R^2NH$ are preferred. These can be synthesized in situ or ex situ, the preparation in situ being preferred for practical reasons. They are prepared from the amine $R^1R^2NH$ and a strong base generally having a $pk_a$ value above 20. Suitable strong bases are organo-alkali-metallic compounds such as phenyl sodium, n-butyl lithium, sec-butyl lithium, methyl lithium, naphthalides of lithium, sodium, or potassium, graphite compounds such as $C_8K$ and $C_{24}K$, and also the hydrides of lithium, sodium, and potassium. Alternatively, the alkali metals themselves can be caused to react with the amines to form the corresponding amides. The alkali metal amides may be used in catalytic and stoichiometric amounts, catalytic amounts being preferably from 0.001 to 0.1 mol per mole of amine. It has been found to be advantageous to pass butadiene into a quantity of a mixture of amine $R^1R^2NH$ and the corresponding amide and to remove the adducts II and III formed, by distillation. Conventional reactors such as bubble-cap columns or loop reactors may be used. Alternatively, a cascade of stirred boilers can be employed. The reaction can be carried out continuously or batchwise. The pressure and temperature ranges involved in this embodiment are the same as those stated above for the reaction of butadiene and amine $R^1R^2NH$ in the presence of a compound of a Group VIIIb element.

Furthermore, the synthesis of the adducts II and III can be effected under the above conditions in the presence of basic metal oxides such as MgO, CaO, SrO, $La_2O_3$, and hydrotalcite. The metal oxides can be used in substance or supported on inert supports.

Instead of using pure 1,3-butadiene there can be used in the process of the invention 1,3-butadiene-containing hydrocarbon streams as raw material. Such streams are produced, for example, as a so-called $C_4$ cut in steam crackers. Advantageously these streams are, prior to use in the process of the invention, relieved of any acetylenic or allenic hydrocarbons contained therein, by partial hydrogenation (Weissermel, Arpe: *Industrielle Organische Chemie;* 3rd Edition, VCH Verlagsgesellschaft, Weinheim 1988). The 1,3-butadiene-containing streams can then be introduced in a similar manner to the pure 1,3-butadiene into the partial reaction a) of the process of the invention. Advantageously the saturated or monoolefinic hydrocarbons contained in these hydrocarbon streams which have not reacted during the reaction taking place in partial reaction a) are removed from the effluent from partial reaction a), for example by means of a gas/liquid separator. The adducts of formulas II and III obtained in the reaction of these streams in partial reaction a) of the process of the invention can be further processed, as described below, to form n-butyraldehyde and/or n-butanol, in the same manner as the adducts II and III produced with pure 1,3-butadiene in reaction a).

The effluent from partial reaction a) of the process of the invention generally contains, in addition to unconverted 1,3-butadiene, the adducts of formulas II and III as well as, possibly, particularly when using transition metal catalysts in partial reaction a), isomers of the respective aminooctadiene, which are referred to below collectively as "aminooctadiene". The aminooctadiene forms by telomerization in a side reaction. In addition to these constituents, the effluent from partial reaction a) can contain small amounts of other by-products, for example, octatriene and vinylcyclohexene. The formation of these by-products can be influenced and if desired minimized by controlling the type of reaction to take place in partial reaction a), for example, by manipulating the 1,3-butadiene-to-amine $R^1R^2NH$ ratio in the reaction mixture, the temperature of reaction, and the pressure.

The adduct required for the preparation of n-butyraldehyde and/or n-butanol in the process of the invention is the 1-aminobutene-2 of formula II, which, for the preparation of the target compounds, can be separated in the process of the invention from its isomer 3-aminobutene-1 of formula III also present in the effluent. Since the adducts II and III are formed in various molar ratios depending on the reaction conditions, the process according to the invention would be uneconomical on an industrial scale, if it were not posible to convert the 3-aminobutene-1 III in an economical manner to the desired 1-aminobutene-2 II.

For this purpose, the adduct III is initially separated from the isomeric adduct II present in the effluent coming from the partial reaction a). This can advantageously be effected by passing the effluent from partial reaction a), after previously removing unconverted 1,3-butadiene, e.g., in a gas-liquid separator or a pressure column, to a distillation apparatus and effecting the desired separation therein by fractional distillation.

This fractional distillation can also be utilized to separate the adduct II from the by-products present in the effluent from partial reaction a), i.e., 1,3-butadiene dimers and trimers. Since these by-products generally have no adverse effect on the rest of the process of the invention, separation thereof can be omitted. Alternatively, the distillation may be operated such that in addition to the adduct III only some of the by-products, particularly the olefinic 1,3-butadiene dimers are separated, whilst other by-products, particularly the aminooctadiene, are processed together with the adduct II in the subsequent partial reactions, the end products formed from these by-products from the partial reaction a) being octanols, which are desirable plasticizer alcohols.

The separation, by distillation, of the readily volatile adduct III from the adduct II can be carried out in a simple manner, e.g., in conventional distillation columns. The adduct III separated from the desired adduct can, as also the unconverted 1,3-butadiene, then be recycled to the partial reaction process stage a) of the process of the invention. Recycling of the adduct III to the process stage defined as the partial reaction a) of the process of the invention causes isomerization of the adduct III to adduct II in this process stage and eventually leads to the suppression of re-formation of the undesirable adduct III, so that when use is made of this recycling method, the overall balance of this cyclic process virtually displays only the desired adduct II and not its undesirable isomer III.

Alternatively, instead of recycling it to the partial reaction process stage a) of the process according to the invention, the adduct III can be isomerized in a separate isomerization process stage by passing the adduct III separated from the adduct II through, e.g., a reactor filled with one of the catalysts suitable for use in partial reaction a), separating the effluent from this reactor, which consists of the isomerization mixture of adduct III and adduct II formed therein, into adduct II and adduct III, for example, by distillation, processing the resulting adduct II to n-butyraldehyde and/or n-butanol in the remaining process stages of the process of the invention and recycling the adduct III back to the isomerization reactor.

The isomerization of the adduct III to the adduct II in the isomerization reactor can take place in the presence or absence of a solvent. It is preferred to carry out this reaction without the use of solvents. If the isomerization is carried out in the presence of a solvent, those used are generally high-boiling solvents such as ethers, for example, di- or tri-ethylene glycol dimethyl ether, di- or tri-ethylene glycol dibutyl ether, high-boiling aromatic or aliphatic hydrocarbons or halogenated aliphatic or aromatic solvents, e.g., dichlorobenzene. The use of low-boiling solvents is possible but usually entails an increase in energy expenditure during distillation of the effluent from the reactor to separate it into the adducts II and III.

In the continuation of the process of the invention for the preparation of n-butyraldehyde and/or n-butanol the adduct II is catalytically isomerized in the partial reaction c) to form the enamine of formula IV, which is then catalytically hydrolyzed in partial reaction d) in the presence of water to form n-butyraldehyde and/or is catalytically converted to n-butanol in the presence of water and hydrogen and/or is hydrolyzed to n-butyraldehyde in the presence of water. The reactions c) and d) in the process of the invention can be effected, as desired, successively in two process stages or successively in a single reactor or, particularly advantageously, as a one-shot process effected in a single process stage. Both reactions c) and d) can take place in the gaseous phase or in the liquid phase.

As just mentioned, the reactions c)—the isomerization of the adduct II to form the enamine IV—and d)—its reaction with water or hydrogen and water to form n-butyraldehyde and/or n-butanol—are carried out in a single process stage or in a number of process stages. As a result, these process stages encompass the following chemical reactions as depicted in the reaction equation (2)

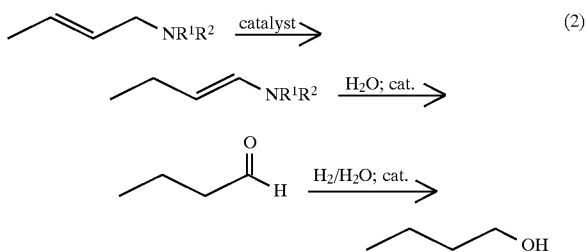

The last reaction step in each case, i.e. the hydrolysis of the enamine IV to n-butyraldehyde on the one hand or the combined hydrolysis/hydrogenation of the enamine IV to n-butanol on the other hand, can, by selecting appropriate reaction conditions, particularly by selecting a suitable catalyst or acid and controlling the amount of the reactants water and hydrogen made available during the reaction, are controlled in such a manner that either the end product n-butyraldehyde or the end product n-butanol is selectively formed or that mixtures of these two desired products are formed as end product of the process of the invention.

We have found, surprisingly, that the catalysts which catalyze the isomerization of the adduct II to the enamine IV, generally also work well as catalysts for the hydrolysis of the enamine IV to n-butyraldehyde or for the combined hydrolysis/hydrogenation of the enamine IV to n-butanol. Accordingly, in a particularly preferred embodiment of the process of the invention, i.e. the execution of the reactions c) and d) in a single process stage, the same catalysts are used both for the preparation of the end product n-butyraldehyde and for the preparation of the end product n-butanol.

Both the isomerization of the adduct II to the enamine IV and the hydrolysis of the enamine IV to n-butyraldehyde or the combined hydrolysis/hydrogenation of the enamine IV to n-butanol can be carried out in the gaseous phase or in the liquid phase. When carrying out these reaction steps in a single process stage in the liquid phase both homogeneous and heterogeneous catalysts can be used. If these process stages are operated in the gaseous phase, heterogeneous catalysts are generally preferred.

The homogeneous catalysts used for the isomerization of the adduct II to the enamine IV and its hydrolysis or combined hydrolysis/hydrogenation to n-butyraldehyde and/or n-butanol in a single process stage comprise a large number of transition metal element compounds, particularly those containing Group VIb, VIIb, and VIIIb elements, preferably chromium, molybdenum, tungsten, rhenium, iron, cobalt, nickel, ruthenium, rhodium, palladium, platinum, osmium, and/or iridium.

Suitable catalysts are, for example, the salts of these transition metals, particularly their halides, nitrates, sulfates, phosphates, or carboxylates soluble in the reaction medium, for example, their $C_1$–$C_{20}$ carboxylates, such as formates, acetates, propionates, 2-ethylhexanoates, and also the citrates, tartrates, malates, malonates, maleates, or fumarates, sulfonates, for example, methanesulfonates, benzenesulfonates, naphthalenesulfonates, toluenesulfonates, or trifluoromethanesulfonates, cyanides, tetrafluoroborates, perchlorates, or hexafluorophosphates, also soluble salts of the oxy-acids of these metals, particularly the alkali metal, alkaline earth metal, or onium salts, such as ammonium, phosphonium, arsonium, or stibonium salts, of vanadium oxy-acids, rhenium oxy-acids, or perrhenic acid, or the anhydrides of these acids, particularly dirhenium heptoxide, soluble inorganic complex compounds of these elements, particularly their aquo, ammine, halo, phosphine, phosphite, cyano, or amino complexes as well as the complexes of these transition metals with chelating agents such as acetylacetone, dioximes, for example, diacetyldioxime, furildioxime, or benzildioxime, ethylenediaminetetraacetic acid, nitrilotriacetic acid, nitrilotriethanol, ureas or thioureas, bisphosphines, bisphosphites, bipyridines, terpyridines, phenanthrolines, 8-hydroxyquinoline, crown ethers or poly(alkylene glycol)s, as well as organometallic compounds of these transition metal elements, for example, carbonyl complexes such as $HRuCl_2(CO)_2(PPh_3)_2$, $RuH_2(CO)(PPh_3)_3$, $HRuCl(CO)(hexyldiphenylphosphine)_3$, $RuH_2(CO)(PPh)_3$, $HRh(CO)(PPh_3)_3$, or $IrCl(CO)(PPh_3)_3$, the abbreviation $PPh_3$ designating triphenylphosphine, also $RuH_2(PPh)_3$, $HRhCl(PPh_3)_3$, $Fe_2(CO)_9$ or $Fe_3(CO)_{12}$, organotrioxorhenium(VII) compounds such as $C_1$–$C_4$ alkyltrioxorhenium(VII), particularly methyltrioxorhenium(VII), cyclopentadienyltrioxorhenium(VII), or phenyltrioxorhenium(VII).

Preferred salt-like homogeneous catalysts are the halides, particularly the chlorides, nitrates, sulfates, carboxylates, and cyanides of rhodium, ruthenium, palladium, platinum, iridium, rhenium, and vanadium as well as the alkali metal, alkaline earth metal, ammonium, alkylammonium, arylammonium, arylphosphonium, and alkylphosphonium salts of vanadic acids, particularly their monovanadates and corresponding salts of rhenic acids, particularly their rhenates(IV), rhenates(VI) and perrhenates.

Another suitable homogeneous catalyst is dirhenium heptoxide ($Re_2O_7$).

Inorganic complex compounds preferably used in the process of the invention for carrying out the reactions c) and d) are, e.g., ruthenium trichloride, rhodium trichloride, and iridium hexaquoditosylate.

Organo-transition-metal element compounds preferably used in the process of the invention as homogeneous catalysts for carrying out the reactions c) and d) are, e.g., carbonyl complexes, such as $HRh(PPh_3)_3(CO)$, $HRuCl(CO)(PPh_3)_3$, or $H_2Ru(CO)_2(PPh_3)_3$, and, very preferably, $RuCl_2(CO)_2(PPh_3)_3$, as well as organotrioxorhenium compounds of the formula V

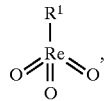

in which $R^1$ is a $C_1$–$C_{10}$ alkyl group, an unsubstituted cyclopentadienyl group or a cyclopentadienyl group substituted by 1 to 5 $C_1$–$C_4$ alkyl groups, a $C_6$–$C_{10}$ aryl group or a $C_7$–$C_{11}$ aralkyl group. For information on the preparation of these organotrioxorhenium compounds reference is made to the processes described in *Angew. Chem.* 100, 420 (1988), *Angew. Chem.* 103, 183 (1991) *J. Organomet. Chem.* 297, C 5(1985), *Angew. Chem.* 100, 1269 (1 988) and *J. Organomet. Chem.* 382, 1 (1990).

Preferred homogeneous catalysts for the execution of the reactions c) and d) in a single process stage are complexes of the transition metal elements mentioned above, particularly those of cobalt, nickel, rhodium, ruthenium, palladium, platinum, and iridium with monodentate or polydentate, particularly bidentate, phosphine or phosphite ligands and/or with nitrogenous ligands, in which the (—N=C—C=N—) structure unit is responsible for their property as chelating agent, for example, 2,2'-bipyridine or 1,10-phenanthroline, as well as the ligands derived from the said heterocyclic compounds by substitution or anellation.

Suitable ligands are, for example, those suitable for carrying out the partial reaction a) of the process of the invention and the phosphine ligands mentioned in this application in the description of said partial reaction, to which reference is made herewith. Examples of suitable 2,2'-bipyridine or 1,10-phenanthroline ligands are those 2,2'-bipyridine or 1,10-phenanthroline ligands mentioned in the description of the partial reaction a) as being suitable for carrying out said partial reaction a) of the process of the invention as well as their derivatives and structural analogs mentioned loc cit, to which reference is made herewith.

Suitable phosphite ligands are, e.g., trialkylphosphites, alkyldiarylphosphites, triarylphosphites, alkylbisphosphites, arylbisphosphites, alkylarylbisphosphites. The alkyl group-carrying ligands may contain the same or different $C_1$–$C_{10}$, preferably $C_1$–$C_6$, alkyl or cycloalkyl groups. The aryl group-carrying ligands can contain the same or different $C_6$–$C_{12}$ aryl groups, particularly the phenyl or naphthyl group, or alternatively the diphenyl group. Furthermore phosphite ligands can be used for complexing the transition metals, which carry heterocycloaliphatic groups, such as pyrrolidine, imidazolidine, piperidine, morpholine, oxazolidine, piperazine, or triazolidine groups or heteroaromatic groups, such as pyrrole, imidazole, oxazole, indole, pyridine, quinoline, pyrimidine, pyrazole, pyrazine, pyridazine, or quinoxazoline groups together with other alkyl or aryl groups. The alkyl or aryl groups of the phosphite ligands can be unsubstituted or can carry substituents which are inert under the conditions of the reaction, such as $C_1$–$C_4$ alkoxy, di-($C_1$–$C_4$ alkyl)amino, $C_1$–$C_6$ alkyl, hydroxy, nitro, cyano, or sulfonate groups. The sulfonate-substituted phosphite ligands and their complexes are generally water-soluble. Suitable phosphite ligands are, e.g., trimethylphosphite, triethylphosphite, tripropylphosphite, triisopropylphosphite, tributylphosphite, tricyclopentylphosphite, tricyclohexylphosphite, triphenylphosphite as well as the mono- and bis-phosphite ligands described in EP-A 472,071, EP-A 213,639, EP-A 214,622, DE-A 2,733,796, EP-A 2261, EP-A 2821, EP-A 9115, EP-A 155,508, EP-A 353,770, U.S. Pat. No. 4,318, 845, U.S. Pat. No. 4,204,997, and U.S. Pat. No. 4,362,830.

When carrying out the reactions c) and d) with catalysts comprising homogeneous phosphine or phosphite complexes soluble in the reaction medium it may be advantageous to add an additional phosphine or phosphite to the reaction mixture, preferably the phosphine or phosphite serving as ligand in the homogeneous catalyst employed. Such an addition can cause prolongation of the useful life of the homogeneous catalyst and moreover improve the selectivity of the isomerization of the adduct II toward the enamine IV and the selectivity in the combined hydrolysis/hydrogenation of the enamine IV to n-butanol and thus the overall selectivity of the process. A similar advantageous effect can be induced by the addition of carbon monoxide to the reaction mixture, particularly when making use of carbonyl group-containing transition metal element complexes as homogeneous catalysts.

Although the addition of hydrogen to the reaction mixture is unnecessary for the synthesis of the end product n-butyraldehyde, the feed of small amounts of hydrogen can, optionally together with the addition of small amounts of carbon monoxide when making use of carbonyl group-containing homogeneous catalysts, lead to a prolongation of the useful life of these homogeneous catalysts. Conveniently, synthesis gas can be used for this purpose.

To achieve the aforementioned effects, the phosphine or phosphite is in general added in a molar amount with respect to the phosphine or phosphite complex of the transition metal element of from 2 to 100 times, preferably from 2 to 20 times and more preferably from 2 to 1 0 times. If the transition metal element complex serving as homogeneous catalyst is produced in situ in the reaction mixture, it is advantageous to use a correspondingly high excess of phosphine or phosphite ligand over the respective transition metal element.

The transition metal catalysts soluble which are homogeneously soluble in the reaction medium are generally employed in amounts of, preferably, from 0.0001 to 0.5 mol %, preferably from 0.0002 to 0.2 mol % with respect to the adduct II fed to the reactor. It will be obvious to the person skilled in the art that the amount of homogeneous catalyst to be added is governed in each case by the catalytical activity of the homogeneous catalyst used. Depending on the nature of the homogeneous catalyst employed it will thus be advantageous to add a larger or smaller amount of catalyst to the reaction mixture. Advantageously the optimum amount is determined in a preliminary test for each homogeneous catalyst to be used.

The execution of the reactions c) and d) in a single process stage with the aid of the said homogeneous catalysts can be carried out batchwise, e.g., in stirred vessels, or continuously, e.g., in tubular reactors or loop reactors, at temperatures of in general from 80° C. to 150° C. and under a pressure of generally from 5 to 100 bar, preferably from 10 to 60 bar. The isomerization of the adduct II to the enamine IV and its conversion to n-butyraldehyde and/or n-butanol in a single process stage can take place in the presence or absence of added solvents, such as aliphatic or aromatic hydrocarbons, e.g., toluene, benzene, or cyclohexane, alcohols, e.g., butanols, particularly n-butanol, higher fatty alcohols or glycols, ethers, e.g., dibutyl ether, tetrahydrofuran, dioxane or low molecular weight poly(alkylene glycol)s, halogenated aliphatic or aromatic hydrocarbons, e.g., chloroform, dichloromethane, chlorobenzene, dichlorobenzene, sulfoxides, or sulfones, e.g., dimethyl sulfoxide or sulfolane.

If no further solvents are added in the single-stage conversion of the adduct II to the end products n-butyraldehyde and/or n-butanol, the reactants themselves, i.e. the adduct II of the enamine IV and the water employed in the invention for the hydrolysis of the enamine IV, and the desired products of the reaction, cause dissolution of the homogeneous catalysts employed in accordance with the invention.

For the preparation of the end products n-butyraldehyde and n-butanol water is added to the reaction mixture in a molar ratio, based on adduct II fed to the reactor, generally of from 1:1 to 100:1 and preferably from 2:1 to 20:1 and more preferably from 3:1 to 10:1. When the process is carried out batchwise the water can be placed in the reactor together with the other reactants, the adduct II and the homogeneous catalyst, but it may be advantageous to meter the water to the reactor following commencement of the reaction. The decision as to which of these modi of operation is to be used will depend on the catalyst used in each case and the pressure and temperature conditions employed. Advantageously the optimum mode of operation is determined for each catalyst used in a preliminary test. Similarly, when the process is carried out continuously, e.g., in a tubular reactor or a cascade of reactors, the water can be passed to the reactor together with the other reactants, or metered to the reactor via a separate inlet only after the reactants have resided in the reactor for a specific period of time.

If the desired end product is n-butanol, not only is water added to the reaction mixture for the hydrolysis of the enamine IV, but also hydrogen is added in a molar ratio, based on adduct II added to the reactor, generally of from 1:1 to 100:1, preferably from 1:1 to 10:1 and more preferably from 1:1 to 3:1. This admixture can take place, when using a batch mode of operation, by forcing in the necessary amount of hydrogen into the reactor or by dispersing the hydrogen in the reaction medium, for example, by means of bubble-cap columns or by means of loop reactors equipped with nozzles for dispersing the hydrogen. The admixture of the hydrogen can take place when the reactor is charged with the other reactants, i.e. the adduct II, the water, and the homogeneous catalyst. Alternatively, the hydrogen can be subsequently introduced into the reaction apparatus, advantageously following commencement of the reaction. The decision as to which of these modi will be used in each instance, will depend on the catalyst used and the pressure and temperature conditions used in each case as well as on the design of the reactor. Conveniently, the optimum mode of operation is determined in a preliminary test. Similarly, when the process is carried out continuously, e.g., in a tubular reactor, a bubble-cap column reactor or a packed column, the hydrogen can be introduced into the reactor together with the other reactants or else fed to the reactants in the reactor through a separate inlet after these have been present therein for a specific period of time.

If the desired end product is a mixture of n-butanol and n-butyraldehyde, the proportions of these products in the product mixture can be controlled, for example via the feed of hydrogen and/or the temperature of reaction used. If substoichiometric amounts of hydrogen are employed, only a portion of the starting material will, of course, be hydrogenated to n-butanol, and by using a lower temperature of reaction the velocity of the hydrogenation reaction can be slowed down to such a degree that only a portion of the starting material is hydrogenated to n-butanol.

Execution of the partial reactions c) and d) in at least two process stages using said homogeneous catalysts may be effected batchwise, e.g. in stirred boilers, or continuously, e.g. in stirred boilers or tubular reactors.

The isomerization of the adduct II to the enamine IV in the first stage can take place in the presence or absence of added solvents, such as aliphatic or aromatic hydrocarbons, e.g., toluene, benzene, or cyclohexane, alcohols, e.g., butanols, particularly n-butanol, higher fatty alcohols or glycols, ethers, e.g., dibutyl ether, tetrahydrofuran, dioxane or low molecular weight poly(alkylene glycol)s, halogenated aliphatic or aromatic hydrocarbons, e.g., chloroform, dichloromethane, chlorobenzene, dichlorobenzene, sulfoxides, or sulfones, e.g., dimethyl sulfoxide or sulfolane.

The isomerization of the adduct II to the enamine IV can be carried out in a phosphine melt instead of in the above conventional solvents. This mode of operation can be used to advantage when phosphine-containing homogeneous catalysts are used. The phosphine then acting as solvent can generally be chosen arbitrarily, but is it preferred to use the same phosphine for the melt as is employed as ligand in the transition metal element complex acting as catalyst.

Then, in the second stage, the hydrolysis of the enamine IV to butyraldehyde or the combined hydrolysis/hydrogenation thereof to form n-butanol can take place using a homogeneous catalyst of the type described above for the single-stage method.

The procedure described for the single-stage process can be employed to obtain n-butyraldehyde and/or n-butanol as desired.

The acids used for the hydrolysis of the enamine IV to butyraldehyde can be, for example, conventional, non-oxidizing Bronsted acids, such as hydrohalic acids, e.g., hydrochloric acid, sulfuric acid, phosphoric acid, perchloric acid, hydrofluoric acid, tetrafluoroboric acid, methanesulfonic acid, or toluenesulfonic acid, or organic acids such as formic acid, acetic acid, propionic acid, or diacids such as oxalic acid. However solid Bronsted acids, particularly organic or inorganic cation exchangers, or acetic or oxalic acid, are preferably employed.

Since the optimum amount of acid to be used varies greatly from acid to acid, the person skilled in the art will have to determine the necessary amount in each case in a preliminary test.

By organic cation exchangers we mean pulverulent, gel-like, or macroporous, polymeric polyelectrolytes, which carry Bronsted acidic functional groups, such as sulfonic or phosphonic acid groups or carboxyl groups, on a polymeric matrix, for example, sulfonated phenol-formaldehyde resins, sulfonated poly(styrene-co-divinyl benzene)s, sulfonated polystyrene, poly(perfluoroalkylenesulfonic acid)s, or sulfonated coals. In the process of the invention these cation exchangers can be used in the form of commercial products such as are available under the trade names Amberlite®, Dowex®, Amberlyst®, Lewatit®, Wofatit®, Permutit®, and Nafion®. Advantageously, the exchangers are used in the process of the invention in their protonized form, the so-called H+ form. Suitable organic cation exchangers are, for example, the commercial products Amberlite® 200, Amberlite® IR 120, Amberlite® IR 132 E, Lewatit® SC 102, Lewatit® SC 104, Lewatit® SC 108, Lewatit® SPC 108, Lewatit® SPC 112, Lewatit® SPC 118 and Amberlyst® 15.

In the process of the invention there may be used, if desired, solids having a Bronsted acid effect instead of said organic acidic cation exchangers, examples of such solids being zeolites, e.g. β-zeolites or Y-type zeolites in the H+ form, bleaching earths such as benonites, montmorillonites, or attapulgites, non-zeolitic molecular sieves on a phosphate basis such as are the subject of U.S. Pat. No. 4,440,871, U.S. Pat. No. 4,310,440, U.S. Pat. No. 4,576,029, U.S. Pat. No. 4,554,143, U.S. Pat. No. 4,500,651, EP-A 158,976, EP-A 158,349, and EP-A 159,624, and also acidic or acid-impregnated metal oxides, the preparation of which is described in U.S. Pat. No. 4,873,017. Preferred Bronsted-acidic inorganic solids are γ-zeolites or Y-type zeolites in their H+ form, particularly γ-zeolites in their H+ form. γ-Zeolites can be prepared, for example, by the method described in U.S. Pat. No. 4,891,458.

When liquid or dissolved Bronsted acid catalysts are used in this partial reaction of the process of the invention, particularly acetic acid or oxalic acid, the procedure adopted is generally as follows: the enamine IV is fed, in liquid form, together with water, to a quantity of the acid and the products formed are removed from the reaction zone by distillation or stripping. This can be effected in conventional reactors such as bubble-cap columns, loop reactors, and the like. It is advantageous to introduce the mixture into the acid via, e.g. jet nozzles. The products may also be separated from the solution of the Bronsted acid in a phase separator. If desired, a cascade of stirred boilers can be used instead of a bubble-cap column or loop reactor.

If, however, solid Bronsted acids are used in the process of the invention in the form of said organic or inorganic catalysts, particularly organic ion exchangers, these are preferably placed in a fixed bed, through which the liquid reaction mixture flows either upwardly or downwardly. The fixed catalyst bed can be installed, for example, in a tubular reactor or, preferably, in a cascade of reactors.

On completion of the reaction, the reaction product is generally purified by distillation, whilst the homogeneous catalyst used is recovered from the bottoms of the distillation to be used again if desired, for example, by recycling the catalyst solution to the process stage involving the isomerization of the adduct II to the enamine IV and its hydrolysis and hydrogenation. If recycling of the catalyst is desired in the process of the invention, a solvent can be added to the reaction mixture, advantageously, this preferably being a solvent which boils at a higher temperature than the reaction products n-butanol and n-butyraldehyde. If the homogeneous catalyst used is chemically and thermally stable under the conditions of the distillation, the addition of a high-boiling solvent can be dispensed with and the homogeneous catalyst can be recycled in solid form to the reaction. When purification is effected by distillation, the reaction product n-butyraldehyde and/or n-butanol is also separated from the amine $R^1R^2NH$ I liberated in the previous process stage from the enamine IV by hydrolysis or hydrogenation, which is recycled to the first process stage of the process of the invention involving the chemical addition of the amine $R^1R^2NH$ I to 1,3-butadiene. Valuable by-products of the process according to the invention can be obtained during purification, by distillation, of the reaction product, these being the octanols, or the aldehydes corresponding to these alcohols, formed as a result of partial dimerization of the butadiene.

In another embodiment of the process of the invention the isomerization of the adduct II to the enamine IV and its hydrolysis or hydrogenation to n-butyraldehyde and/or n-butanol is carried out in a single process stage using a heterogeneous catalyst, whilst the process can be carried out either in the liquid phase or in the gaseous phase.

We have found, surprisingly, that the catalysts that can be used both for the isomerization of the adduct II to the enamine IV and for the hydrolysis of the enamine IV to n-butyraldehyde or for the combined hydrolysis/ hydrogenation of the enamine IV to n-butanol are commonly used heterogeneous hydrogation catalysts substantially insoluble in the reaction medium. Of these hydrogenation catalysts those are preferred which contain one or more Group Ib, VIb, VIIb, and VIIIb elements, optionally in combination with one or more Group Vb elements, particularly copper, chromium, molybdenum, tungsten, rhenium, ruthenium, cobalt, nickel, rhodium, iridium, palladium, and/or platinum, optionally in combination with iron.

The more active hydrogenation catalysts such as nickel or the platinum metals can be advantageously doped with main group elements capable of acting as catalyst poisons, so as to partially poison such catalysts. This makes it possible to achieve a higher degree of selectivity in the combined hydrolysis/hydrogenation of the enamine IV to n-butanol. Suitable main group elements are, e.g., the chalcogenes, such as sulfur, selenium, and tellurium, as well as the elements phosphorus, arsenic, antimony, bismuth, tin, lead, and thallium.

In the process of the invention use can be made of, e.g., so-called precipitation catalysts to act as the heterogeneous catalysts. Such catalysts can be prepared by precipitating their catalytically active components in the form of, e.g., difficultly soluble hydroxides, oxide hydrates, basic salts, or carbonates from their salt solutions, particularly from solutions of their nitrates and/or acetates, for example, by the addition of solutions of alkali metal and/or alkaline earth metal hydroxides and/or carbonates, then drying the precipitates obtained and converting them, by calcination at generally from 300° to 700° C., particularly from 400° to 600° C., to the respective oxides, mixed oxides and/or oxides of mixed-valency, which are reduced, e.g., by treatment with reducing agents, such as hydrogen or hydrogen-containing gases, at usually from 20° to 700° C., particularly at a temperature of from 20° to 300° C., to the respective metals and/or oxidic compounds having a low degree of oxidation and are thus converted to the actual catalytically active form. During this process reduction is usually carried out until no more water is formed. In the preparation of precipitation catalysts containing a support material, the precipitation of the catalytically active components can take place in the presence of the respective support material. Alternatively however, the catalytically active components can be advantageously precipitated concurrently with the support material from the respective salt solutions.

In the process of the invention it is preferred to use hydrogenation catalysts in which the metals or metal compounds catalyzing the hydrogenation are present as deposits on a support material. Apart from the aforementioned precipitation catalysts containing a support material in addition to the catalytically active components, suitable catalysts for the process of the invention are generally those supported catalysts in which the catalytically effective components have been applied to a support material by, say, impregnation.

The manner in which the catalytically active metals are applied to the support is not usually important and can comprise a wide variety of methods. The catalytically active metals can be applied to these support materials, e.g., by impregnation with solutions or suspensions of the salts or oxides of relevant elements, drying and then reducing the metal compounds to the respective metals or compounds of a lower degree of oxidation by means of a reducing agent, preferably with the aid of hydrogen, hydrogen-containing gases or hydrazine. Another possibility to effect application of the catalytically active metals on to these supports consists in impregnating the supports with solutions of thermally readily decomposable salts, e.g., with nitrates or with thermally readily decomposable complex compounds, e.g., carbonyl or hydrido complexes of the catalytically active metals, and heating the impregnated support to temperatures of from 300° to 600° C. for the purpose of thermally decomposing the adsorbed metal compounds. This thermal decomposition is preferably carried out under a blanket of protective gas. Suitable protective gases are, e.g., nitrogen, carbon dioxide, hydrogen, or the noble gases. Furthermore the active metals can be deposited on to the catalyst support by vapor deposition or by flame spraying.

The content of catalytically active metals in these supported catalysts is theoretically irrelevant to the success of the process according to the invention. It will be apparent to the person skilled in the art that higher contents of catalytically active metals in these supported catalysts lead to higher space-time yields than lower contents. Generally however, supported catalysts are used whose content of catalytically active metals is from 0.1 to 80wt % and preferably from 0.5 to 30wt %, based on the total catalyst. Since these content data refer to the total catalyst including support material, and since different support materials have very different specific weights and specific surface areas, these statements can be deviated from upwardly or downwardly without impairing the results of the process of the invention. Of course, a number of catalytically active metals can be applied to the respective support material if desired. Furthermore the catalytically active metals can be applied to the support, for example, by the processes described in DE-A 2,519,817, EP-A 147,219, and EP-A 285,420. In the catalysts described in the aforementioned references the catalytically active metals are present in the form of alloys, which are produced by thermal treatment and/or reduction of salts or complexes of the above metals deposited on a support by, e.g., impregnation. Activation of the precipitation catalysts and of the supported catalysts can also take place in situ in the reaction mixture due to the hydrogen present therein, however, these catalysts are preferably activated prior to use in the process of the invention.

Suitable support materials are generally the oxides of aluminum and titanium, zirconium dioxide, silicon dioxide, kieselguhr, silica gel, argillaceous earths, e.g., montmorillonites, silicates, such as magnesium or aluminum silicates, zeolites, such as ZSM-5 or ZSM-10 zeolite, and activated charcoal. Preferred support materials are aluminum oxides, titanium dioxides, zirconium dioxide, and activated charcoal. It is of course possible to use mixtures of different support materials as supports for catalysts to be used in the process of the invention, if desired.

Examples of suitable heterogeneous catalysts for execution of the reactions c) and d) in a single process stage are the following catalysts:
platinum dioxide, palladium on aluminum oxide, palladium on silicon dioxide, palladium on barium sulfate, rhodium on activated charcoal, rhodium on aluminum oxide, ruthenium on silicon dioxide or activated charcoal, nickel on silicon dioxide, cobalt on silicon dioxide, cobalt on aluminum oxide, carbonyliron powder, rhenium black, Raney rhenium, rhenium on activated charcoal, rhenium/palladium on activated charcoal, rhenium/platinum on activated charcoal, copper on kieselguhr, copper on silica gel, copper on titanium dioxide, copper on zirconium dioxide, copper on magnesium silicate, copper on aluminum silicate, copper on montmorillonite, copper on zeolite, Raney copper, platinum oxide/rhodium oxide mixtures, platinum/palladium on activated charcoal, copper chromite, barium chromite, nickel/chromium oxide on aluminum oxide, dirhenium heptoxide (Re$_2$O$_7$), cobalt sulfide, nickel sulfide, molybdenum(VI) sulfide, copper/molybdenum(VI) oxide/silicon dioxide/ aluminum oxide catalysts, palladium on activated charcoal catalysts partially poisoned with selenium or lead, and the catalysts described in DE-A 3,932,332, U.S. Pat. No. 3,449, 445, EP-A 44,444, EP-A 147,219, DE-A 3,904,083, DE-A 2,321,101, EP-A 415,202, DE-A 2,366,264, and EP-A 100, 406.

It may be advantageous to use, in the process of the invention, hydrogenation catalysts containing Brönsted and/ or Lewis acid centers. When using such catalysts the further addition of a Brönsted or Lewis acid to the reaction mixture is generally unnecessary.

The catalytically active metals themselves can act as Brönsted or Lewis acid centers if, for example when effecting activation of the catalyst with hydrogen or hydrogenous gases, reduction to the respective metals is not carried to completion. This applies, e.g., to rhenium-containing and chromite-containing catalysts, such as supported rhenium catalysts and copper chromite. In the supported rhenium catalysts the rhenium is present in the form of a mixture of rhenium metal with rhenium compounds at higher oxidation stages, where the latter can display effects such as those shown by Lewis or Brönsted acids. Moreover, such Lewis or Brönsted acid centers can be introduced into the catalyst via the support material used. As support materials containing Lewis or Brönsted acid centers there may be mentioned, e.g., titanium dioxides, zirconium dioxide, silicon dioxide, the silicates, argillaceous earths, zeolites, and activated charcoal.

Thus we particularly prefer to use, in the process of the invention, as hydrogenation catalysts, supported catalysts which contain Group Ib, VIb, VIIb, and/or VIIIb elements, particularly Group Ib, VIIb, and VIIIb elements deposited on a Brönsted or Lewis-acid support material. Particularly advantageous catalysts are, e.g., rhenium on activated charcoal, rhenium on zirconium dioxide, rhenium on titanium dioxide, rhenium on silicon dioxide, copper on activated charcoal, copper on silicon dioxide, copper on kieselguhr, copper on silica gel, copper on titanium dioxide, copper on zirconium dioxide, copper on magnesium silicate, copper on aluminum silicate, copper on bleaching earth, copper on zeolite, ruthenium on activated charcoal, ruthenium on aluminum oxide, ruthenium on silicon dioxide, ruthenium on titanium dioxide, and also palladium on activated charcoal catalysts partially poisoned with selenium or lead.

Hydrogenation catalysts, which do not themselves have such Brönsted or Lewis acid centers, can be admixed with Lewis or Brönsted acidic components, such as zeolites, aluminum or silicon oxides, phosphoric acid or sulfuric acid. The latter are generally added in amounts of from 0.01 to 5 wt %, preferably from 0.05 to 0.5 wt % and more preferably from 0.1 to 0.4 wt %, based on the weight of the catalyst.

Other suitable heterogeneous catalysts for the isomerization of the adduct II to the enamine IV and its hydrolysis or hydrogenation to n-butyraldehyde and/or n-butanol in a single process stage are those which contain in heterogenized form the complex compounds of Group VIb and VIIIb transition metal elements which can be used for the homogeneous catalysis of the complex compounds suitable for use in this process stage, for example, those in which the respective transition metal element is attached to a polymeric matrix.

Such polymeric matrices can be resins, such as styrenedivinylbenzene resins (U.S. Pat. No. 3,725,489) or phenolformaldehyde resins, to which the respective ligands serving to chelate the transition metal element are preferably attached by covalent bonds, which again form complexes with the respective transition metals and thus quasi immobilize them. Such heterogenized, polymerically linked transition metal element complex catalysts with 2,2'-bipyridine or 1,10-phenanthroline ligands or heterogenized phosphine or phosphite complexes of the catalytically active transition metal elements can be prepared, e.g., by the prepublished processes mentioned above for the preparation of said catalysts in connection with the description of partial reaction a). Organotrioxorhenium(VII) catalysts can, e.g., be attached by coordinate-bond linkage, by the process described in DE-A 3,902,357, to nitrogenous polymers, such as poly(vinyl pyrrolidone), poly(2-vinylpyridine), poly(2-vinylpyridine-co-styrene), poly(acrylic acid amide)s, polyimides, polyamides, and polyurethanes and heterogenized in this way, and then used in the process of the invention as heterogeneous catalysts.

Using the said heterogeneous catalysts the isomerization of the adduct II to the enamine IV and its hydrolysis or hydrogenation to n-butyraldehyde and/or n-butanol can be carried out in a single process stage continuously or batchwise.

If this reaction is carried out in the liquid phase, the heterogeneous catalyst can be used in the form of suspended solids in the liquid reaction medium or, preferably, in the form of a fixed bed or a number of fixed beds. When use is made of a heterogeneous catalyst suspended in the liquid reaction medium the process can be carried out, e.g., in stirred vessels or loop reactors. When use is made of a heterogeneous catalyst in the form of a fixed bed the reaction mixture is in general passed through the fixed catalyst bed either upwardly or downwardly.

Both the hydrogenation of the enamine IV and its hydrolysis or hydrogenation can be carried out in adiabatic or isothermal reactors. Generally the space velocity of the liquid reaction mixture relatively to the catalyst is equivalent to from 0.01 to 10, preferably from 0.05 to 3 and more preferably from 0.08 to 1 kg of amine per liter of catalyst per hour. When use is made of the heterogeneous catalysts the reaction can take place in the presence or absence of a solvent. Suitable solvents are the same as those which can be used when carrying out the process under homogeneous catalysis conditions.

As described above with reference to carrying out the reactions c) and d) of the process of the invention using homogeneous catalysis, the water required for the preparation of the end products n-butyraldehyde and/or n-butanol can be fed to the reactor together with the adduct II and/or added via separate feed lines, divided into one or more partial streams, and introduced into the catalyst bed at various points. The same applies to the feed of water and hydrogen for the preparation of the end product n-butanol.

The water required for the preparation of n-butyraldehyde when carrying out the process under heterogeneous catalysis conditions is fed to the reactor at such a rate that the molar ratio of water to the adduct II added is generally from 1:1 to 100:1, preferably from 1:1 to 50:1 and more preferably from 1:1 to 10:1. The combined isomerization of the adduct II to the enamine IV and its hydrolysis to n-butyraldehyde in a single process stage over a heterogeneous catalyst in the liquid phase is generally carried out at a temperature of from 20° to 400° C., preferably from 30° to 300° C. and more preferably from 80° to 200° C. and under a pressure of, in general, from 1 to 300 bar, preferably from 2 to 1 50 bar, and more preferably from 5 to 100 bar.

The hydrogen required, in addition to water, for the preparation of n-butanol when carrying out the process under heterogeneous catalysis conditions is fed to the reactor at such a rate that the molar ratio of hydrogen added to adduct II added is generally from 1:1 to 100:1, preferably from 1.5:1 to 80:1, and more preferably from 2:1 to 40:1. The combined isomerization of the adduct II to the enamine IV and its hydrolysis/hydrogenation to n-butanol in a single process stage in a heterogeneous catalyst system in the liquid phase is generally carried out at a temperature of from 20° to 400° C., preferably from 30° to 300° C. and more preferably from 80° to 200° C. and under a pressure of generally from 1 to 300 bar, preferably from 5 to 250 bar, and more preferably from 20 to 200 bar. Of course, the quantity of water required for the preparation of n-butanol from the adduct II is the same as that required for the preparation of n-butyraldehyde from the adduct II.

If the desired end product is a mixture of n-butyraldehyde and n-butanol, water and hydrogen are introduced at rates similar to those mentioned above and relate to the rate of feed of the adduct II such that the isolation of the two end products in the desired ratio of the products is possible. Moreover the ratio of these two end products in the effluent can also be controlled by using different heterogeneous catalysts, for example, by using heterogeneous catalysts which possess high hydrolysis activity and, in comparison, relatively low hydrogenation activity. This purpose can be advantageously realized, for example, by using catalysts that have been inactivated or partially poisoned with regard to their hydrogenating properties, e.g., palladium on activated charcoal catalysts partially poisoned with selenium or lead.

The liquid effluent from this process stage is generally worked up by distillation, in a manner similar to that described above with reference to the execution of this process stage using homogeneous catalysts. Of course recycling of the catalyst, which may possibly be convenient and advantageous when using homogeneous catalysts, is omitted when using heterogeneous catalysts. Recycling of the amine $R^1R^2NH$ I liberated in this process stage back to the process stage involving the addition of the amine $R^1R^2NH$ I to 1,3-butadiene can be advantageously carried out in a manner similar to that already described with reference to the reaction occurring in this process stage using homogeneous catalysts.

As already mentioned, the isomerization of the adduct II to the enamine IV and its hydrolysis or hydrogenation to n-butyraldehyde and/or n-butanol in a single process stage can be advantageously carried out in the gaseous phase. To this end conventional reactors for gas phase reactions are used, for example, those in which the catalyst is in the form of a fixed bed or fluidized bed. The reactors can be operated adiabatically or isothermally. When use is made of a fixed bed catalyst system, the catalyst can be disposed in a single fixed bed or, advantageously for the purpose of improving the dissipation of the heat of reaction, in a number of fixed beds, for example, in from 2 to 10 and preferably from 2 to 5 fixed beds. When making use of a number of fixed catalyst beds or when employing an adiabatic mode of operation of the reactor it may be advantageous to use intra-bed cooling of the reaction gas and/or to effect a temperature decrease of the reaction gas as it leaves one bed but before it reaches the next bed by injecting additional amounts of cool reactants such as hydrogen, water, adduct II, or enamine IV between the individual fixed beds, in order to increase the selectivity of the reaction. Heat dissipation may also be effected by circulating the gas. Advantageously, when use is made of a number of fixed beds, the reaction in the individual fixed beds except for the last fixed bed is only allowed to reach partial conversion, for example, a conversion of from 50 to 98%. The reaction gases can be diluted if desired with a gas inert under the reaction conditions, such as nitrogen, saturated hydrocarbons, or argon.

The water required for the preparation of the end product n-butyraldehyde when carrying out the process in the gaseous phase is metered into the reactor at a rate in relation to the rate of input of the adduct II such that the molar ratio of water added to adduct II added is generally from 1:1 to 100:1, preferably from 1:1 to 50:1 and more preferably from 1:1 to 10:1. The water can be fed to the reactor together with the adduct II and/or, as described above, divided into a number of partial streams and introduced at different points of the reactor. Generally the space velocity of the reaction gas, essentially containing the adduct II, water, and if desired an inert gas, is from 0.01 to 10, preferably from 0.05 to 3 and more preferably from 0.07 to 1 kg of reaction gas per liter of catalyst per hour. The reaction, encompassing the isomerization of the adduct II to the enamine IV and its hydrolysis, is generally carried out at a temperature of from 70° to 400° C., preferably from 90° to 350° C. and more preferably from 110° to 230° C. and under a pressure of in general from 0.5 to 100 bar, preferably from 0.8 to 20 bar and more preferably from 1 to 10 bar.

The hydrogen required for the preparation of the end product n-butanol in addition to water, when carrying out the process in the gaseous phase, is fed to the reactor at a rate relative to the rate of feed of the adduct II such that the molar ratio of hydrogen added to adduct II added is in general from 1:1 to 200:1, preferably from 1.5:1 to 80:1 and more preferably from 2:1 to 30:1. Hydrogen can be fed to the reactor together with the adduct II and/or, as described above, divided into a number of partial streams and fed in at various points of the reactor. Generally the space velocity of the reaction gas, essentially containing the adduct II, water, hydrogen, and if desired an inert gas, is from 0.01 to 10, preferably from 0.05 to 3, more preferably from 0.07 to 1 kg of reaction gas per liter of catalyst per hour. The reaction, encompassing the isomerization of the adduct II to the enamine IV and its combined hydrolysis/hydrogenation, is generally carried out at temperatures of from 20° to 400° C., preferably from 100° to 350° C. and more preferably from 150° to 250° C. and under a pressure generally of from 0.5 to 100 bar, preferably from 0.9 to 30 bar, and more preferably from 1 to 10 bar.

In a manner similar to that described above with reference to the isomerization of the adduct II to the enamine IV and its hydrolysis or hydrogenation to n-butyraldehyde and/or n-butanol in the liquid phase using heterogeneous catalysts, the reaction in the gaseous phase can be controlled by the feed of a mixture containing specific amounts of water and hydrogen, and by selecting the catalyst to be used such that the effluent from this process stage contains n-butyraldehyde and n-butanol in the desired proportions.

In order to work up the gaseous effluent it is advantageous to pass this, optionally after depressurization to atmospheric pressure, directly to a distillation apparatus where it is separated by distillation into its constituent parts.

The catalysts that can be used for the isomerization of the adduct II to the enamine IV and its hydrolysis or hydrogenation to n-butyraldehyde and/or n-butanol in the gaseous phase in a single process stage are basically the same heterogeneous catalysts as those employed in the same reaction in the liquid phase. Preferably purely inorganic, mineral catalysts are used in the gas phase process. Preferred catalysts are, for example, supported catalysts containing Group Ib, VIb, VIIb, and/or VIIIb elements, optionally in combination with one or more Group Vb elements, particularly Group Ib, VIIb, and VIIIb elements present as deposits on a Bronsted or Lewis acid support material. Particularly advantage ous catalysts are, e.g., rhenium on titanium dioxide, rhenium on silicon dioxide, copper on activated charcoal, copper on silicon dioxide, copper on kieselguhr, copper on silica gel, copper on titanium dioxide, copper on zirconium dioxide, copper on magnesium silicate, copper on aluminum silicate, copper on bleaching earth, copper on zeolite, ruthenium on activated charcoal, ruthenium on silicon dioxide, ruthenium on aluminum oxide, ruthenium on zirconium dioxide, ruthenium on magnesium oxide, and ruthenium on titanium dioxide, and also palladium on activated charcoal catalysts partially poisoned with selenium or lead.

A further advantageous embodiment of the isomerization of the adduct II to the enamine IV and its hydrolysis or hydrogenation to n-butyraldehyde and/or n-butanol in a single process stage using heterogeneous catalysts can be achieved both when use is made of the liquid phase process and when use is made of the gas phase process and when making use of a single fixed bed for carrying out these reactions, by employing a combined catalyst bed, consisting of at least 2 layers of different heterogeneous catalysts which differ in activity and possibly selectivity for the two reactions c) and d), such that, e.g., in the first layer, i.e. that nearest the reactor inlet, the adduct II is initially isomerized with high activity and selectivity to the enamine IV, which then on passing through the next layer or layers, i.e. that or those nearest the outlet of the reactor and containing catalysts having lower isomerization activity but higher hydrolysis activity and/or higher hydrogenation activity is converted to n-butyraldehyde and/or n-butanol at a high degree of activity and selectivity.

By using a number of contiguous layers of variously active and/or selective catalysts it is possible to achieve accurate control of the heat generated during hydrolysis or the combined hydrolysis/hydrogenation of the enamine IV, by which means the overall selectivity of the reaction can be increased. This effect can be intensified by e.g., introducing the reactants water and/or hydrogen into the reactor separately from the adduct II at that zone of the catalyst bed where the hydrolysis or the combined hydrolysis/hydrogenation takes place. The water and the hydrogen can be passed together to the respective zones of the catalyst bed or alternatively individually to different zones of the catalyst bed. Instead of using a combined bed containing all of the different catalysts required for catalyzing the individual reactions, it is possible, in this embodiment, to have the catalysts present in a number of fixed beds, each containing a different catalyst.

Although the execution of the reactions c) and d) of the process according to the invention in a single process stage, e.g., by the methods described above is a preferred embodiment of the process of the invention, it may be advantageous under certain circumstances to carry out the individual reactions, i.e. the isomerization of the adduct II to the enamine IV, the hydrolysis of the enamine IV to n-butyraldehyde or the hydrogenation of the butyraldehyde to n-butanol, in a number of process stages. For example, it is possible to carry out each one of these reactions in an individual process stage by first isomerizing the adduct II to the enamine IV in one process stage, then hydrolyzing the enamine IV to n-butyraldehyde and then hydrogenating the n-butyraldehyde to n-butanol, or separating the resulting butyraldehyde or a portion of said butyraldehyde and aldolizing the same in a further stage followed by hydrogenation to 2-ethylhexanol. Such process steps are well known to the person skilled in the art. Likewise the isomerization of the adduct II to the enamine IV can take place in a separate process stage and the enamine IV can then be hydrolyzed to n-butyraldehyde or be further processed in a hydrolysis/hydrogenation reaction to n-butanol or a mixture of n-butanol and n-butyraldehyde. A further variant of the process according to the invention comprises carrying out the isomerization of the adduct II to the enamine IV and its hydrolysis to n-butyraldehyde in a single process stage and then hydrogenating the n-butyraldehyde thus obtained to n-butanol in a further process stage.

When the partial reactions c) and d) are distributed over a number of process stages a wide variety of operational modi can be used in the individual process stages. For example, the isomerization of the adduct II to the enamine IV can be carried out as desired under homogeneous catalysis conditions or over heterogeneous catalysts. Also the hydrolysis or the combined hydrolysis/hydrogenation of the enamine IV to n-butyraldehyde and n-butanol can be carried out either: in the liquid phase using homogeneous catalysts or heterogeneous catalysts or: in the gaseous phase.

When the individual partial reactions c) and d) are distributed over a number of process stages it is also possible to use, in the individual process stages, instead of the catalysts described above, which catalyze both the isomerization of the adduct II to the enamine IV and its hydrolysis and hydrogenation, catalysts which can catalyze only the respective partial reaction. Thus the enamine IV can be hydrolyzed, for example, by means of Bronsted acid catalysts, such as mineral acids, e.g., hydrohalic acids, sulfuric acid, dilute nitric acid, phosphoric acid, or heterogeneous Brönsted acids, such as ion exchangers, zeolites, bleaching earths, or acid phosphates, for example, aluminum phosphates, to n-butyraldehyde. In this case the amine is liberated from its acid salt by the additon of a base.

The amine $R^1R^2NH$ I liberated during hydrolysis or combined hydrolysis/hydrogenation of the enamine IV is preferably recycled back to the reaction defined as partial reaction a). On account of the possibility of splitting up the partial reactions of the isomerization of the adduct II to the enamine IV and its hydrolysis or its combined hydrolysis/hydrogenation into a number of process steps, a higher degree of flexibility is obtained when designing a plant for carrying out the process of the invention, by which means considerable savings can be effected.

The n-butyraldehyde produced in the process of the invention can, after it has been isolated by, say, distillation, be converted to 2-ethylhexanol in known manner. Thus n-butyraldehyde may be converted to the aldol product 2-ethylhex-2-enal at 80° to 130° C. and 3–10bar in the presence of sodium or potassium hydroxide. This aldol product can then be catalytically reduced to 2-ethylhexanol at approximately 200° to 250° C. and 50–200 bar of hydrogen.

Alternatively, a reaction mixture produced by the process of the invention and containing n-butyraldehyde can be subjected to aldolization and hydrogenation in the manner described above and the product can be distilled to isolate it from the impurities present in the original reaction mixture.

The embodiment is preferred in which the butyraldehyde is prepared by acid hydrolysis of the enamine IV, as described in detail above. In the presence of the acid present in the reaction mixture, the n-butyraldehyde can react to form the aldol product 2-ethylhex-2-enal. While it is desirable to suppress this reaction when n-butyraldehyde is the desired product, the reaction can be manipulated to ensure that the aldol reaction preferentially occurs. This usually necessitates longer reaction times under otherwise identical reaction conditions. Alternatively, the reaction producing the aldol product can be accelerated by increasing the temperature or the concentration of acid over that required when the process is operated to give a high yield of n-butyraldehyde. Due to the wide range of possibilities available in the preparation of n-butyraldehyde the person skilled in the art will have to carry out preliminary tests to determine the best reaction conditions for attaining high yields of aldol product. The resulting aldol product can be hydrogenated to 2-ethylhexanol by conventional methods. The overall reaction yielding 2-ethylhexanol is effected in a particularly advantageous manner when the catalyst used in process stage c) of the process of the invention for the preparation of n-butyraldehyde and/or n-butanol is a homogeneous catalyst, e.g., a ruthenium catalyst, which is also capable of catalyzing the hydrogenation to take place in process stage d), provided that the hydrolysis of the enamine IV is carried out in the presence of an acid and process stage d) is carried out in the presence of hydrogen as described above for the preparation of n-butanol. In such a case the conversion of the anamine IV to 2-ethylhexanol can be effected in a single stage. Purification and recycling of the amine I can be carried out in a manner similar to that described above for the preparation of n-butanol.

Process stage a)

EXAMPLES 1 TO 7

Example 1

Partial Reaction a)

A steel autoclave having a capacity of 0.3 L was filled with 0.50 mol of the appropriate amine, 1.25 mol of palladium acetylacetonate, and 2.5 mmol of phosphine ligand, and the respective amount of butadiene was then forced into the recator. The reaction mixture was stirred at 145° C. under the autogenous pressure of the system. On completion of the reaction, the liquid effluent was analyzed by gas chromatography (Carbowax 20 M, 2 m (percentages by area based on amine)).

bis(di-tert-butylphosphino)methane and then 2.70 g (50 mmol) of butadiene were forced in. Following a reaction time of 5 h at 80° C. and autogenous pressure there was obtained a yield of 75% at a selectivity of 1 percent by area of octatriene, 6 percent by area of (3,N)-(but-1-enyl)-morpholine, 76 percent by area of (1,N)-(but-2-enyl) morpholine, 10 percent by area of octadienylmorpholine and 1 percent by area of by-products, as determined by gas chromatographic analysis.

Example 9

A solution of 8.70 g (100 mmol) of morpholine, 0.076 (0.25 mmol) of Pd(acac)$_2$ (acac=acetylacetonate), and 0.35 g (0.875 mmol) of DPPE was admixed with 0.141 g of p-toluenesulfonic acid and 2.4 g of methanol. After forcing in 5.4 g (100 mmol) of butadiene, the mixture was stirred for 17 h at 100° C. under autogenous pressure. There is obtained a yield of 96% at a selectivity of 1 percent by area of octatriene, 3 percent by area of (3,N)-(but-1-enyl) morpholine, 94 percent by area of (1,N)-(but-2-enyl)-morpholine, 1 percent by area of octadienylamine and 1 percent by area of by-products.

Process stage c)

Example 10

A solution of 3.06 g (21.7 mmol) of (1,N)-(but-2-enyl)-morpholine, 0.023 g (0.024 mmol) of HRuCl(CO)(PPh$_3$)$_3$ and 0.034 g (0.125 mmol) of triphenylphosphine was admixed with 20 g of water and the mixture was stirred at 12 bar of hydrogen and 150° C. Following a reaction period of 20 h there was obtained a yield of 90% at a selectivity of 64 percent by area of 1-butanol, 4 percent by area of (1,N)-(but-1-enyl)morpholine and 32 percent of N-butylmorpholine, as determined by gaschromatographic anaylsis. The morpholine was recovered.

Example 11

Under a blanket of argon, 19 g (122 mmol) of (1,N)-(but-2-enyl)-morpholine were caused to react in a melt of 30 g (114 mmol) of triphenylphosphine and 1.5 g (1.63 mmol) of

TABLE

| | | | | | Selectivity [%]* | | | | |
|---|---|---|---|---|---|---|---|---|---|
| Ex. | Amine | Ligand | Butadiene [mmol] | Reaction time[h] | Yield [%] | 3,N-But-1-enylamine III | 1,N-But-2-enylamine II | 3,N-Octa-dienylamine | 1,N-Octa-dienylamine | By-pro ducts |
| 1 | Morpholine | DPPB | 706 | 20 | 97 | 3 | 64 | 1 | 21 | 11 |
| 2 | Morpholine | DPPP | 740 | 20 | 82 | 4 | 72 | 1 | 20 | 3 |
| 3 | Morpholine | DPPE | 747 | 20 | 94 | 3 | 64 | 1 | 21 | 11 |
| 4 | Piperidine | DPPE | 736 | 20 | 90 | 3 | 80 | 0 | 12 | 5 |
| 5 | Piperidine | DPPE | 510 | 20 | 79 | 4 | 79 | 0 | 14 | 3 |
| 6 | Piperidine | DPPE | 488 | 10 | 76 | 4 | 80 | 0 | 13 | 3 |
| 7 | Dipropyl-amine | DPPE | 769 | 20 | 67 | 3 | 64 | 0 | 25 | 8 |

DPPE = bis(diphenylphosphino)ethane
DPPP = bis(diphenylphosphino)propane
DPPB = bis(diphenylphosphino)butane
*based on amine, percentage by area Example 8

To a solution of 0.12 g (0.25 mmol) of [bis(di-tert-butylphosphino)methane]palladium dichloride in 4.36 g (50 mmol) of morpholine there were added successively 0.107 g (0.55 mmol) of AgBF$_4$ und 0.076 g (0.25 mmol) of HRh(PPh$_3$)$_3$CO over a period of 245 min at 120° C. with stirring. The products were then removed by distillation under reduced pressure (15 mbar) and a temperature of up to 120° C. and analyzed by gas chromatography. The following results were achieved: the yield of (1,N)-(but-2-enyl)- morpholine was 98.1%, apart from (1,N)-(but-1-enyl) morpholine no other product was found (selectivity 100%).
Process stage d)

Example 12

2 g (15.9 mmol) of (1,N)-(but-1-enyl)-morpholine were heated with 5 g (278-mmol) of water in the presence of 14 g of 1.4-dioxane and 0.5 g of Bayer Catalyst No. 2611 (acid ion exchanger) for 4 h to a temperature of 120° C. The two liquid phases of the original mixture become a single phase. GC analysis showed a yield of 75% at a selectivity of 31 percent by area of n-butyraldehyde and 69 percent by area of 2-ethylhex-2-enal. morpholine was recovered.
Process stages c) and d)

Example 13

30 g (50 mL) of a copper-on-silica-gel catalyst having a copper content (calculated as CuO) of 26 wt %, were placed in a reactor, and the catalyst was activated over a period of 18 h with forming gas (5% hydrogen, 95% nitrogen) at atmospheric pressure and a temperature starting from 30° C. and reaching a final value of 190° C. Following activation the gas flow was switched to pure hydrogen.

1.5 g/h of water and 2.75 g/h of (1,N)-(but-2-enyl)-morpholine were then fed, at atmospheric pressure, to the reactor held at 190° C. via a preheater held at 150° C. At the same time a hydrogen stream of 8 L/h was passed into the reactor. Following cooling, the single-phase liquid effluent was analyzed by gas chromatography. At a yield of 60% there was achieved a selectivity of 54 percent by area of 1-butanol, 4 percent by area of (1,N)-(but-1-enyl)-morpholine and 42 percent by area of N-butylmorpholine.

We claim:

1. A process for the preparation of n-butyraldehyde and/or n-butanol, wherein a) 1,3-butadiene is caused to react with an amine of the formula I

   I in which $R^1$ and $R^2$ independently denote hydrogen, optionally substituted aliphatic or cycloaliphatic radicals, or aryl or aralkyl radicals or are linked to form a nitrogen-containing bridging member, which bridging member can contain an additional nitrogen atom and/or oxygen atom, the number of bridging atoms being from 3 to 6 at elevated temperature and under superatmospheric pressure in the presence of a compound of a Group VIIIb element to form a mixture of the adducts of the formulas II

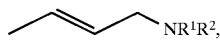   II and III

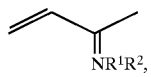   III b) the adduct III is isomerized to the adduct II
c) the adduct II is isomerized in the presence of a homogeneous or heterogeneous transition metal element catalyst in the liquid phase or in the presence of a heterogeneous catalyst containing a transition metal element in the gaseous phase to form the enamine of the formula IV

   IV and d) n-butyraldehyde and/or n-butanol is/are produced from this enamine IV by the reaction thereof with hydrogen and water or water only in the presence of a homogeneous or heterogeneous transition metal element catalyst in the liquid phase or in the presence of a heterogeneous transition metal element catalyst in the gaseous phase, in the presence of an acid or in the presence of one of said catalysts and an acid, and the amine I is liberated, and the liberated amine I is recycled to the stage defined above as reaction a).

2. A process as defined in claim 1, wherein the reaction of 1,3-butadiene with an amine $R^1R^2NH$ I is carried out in the presence of a catalyst comprising an alkyl, aryl, or arylalkyl phosphine complex of rhodium, ruthenium, nickel, palladium, iridium, or platinum.

3. A process as defined in claim 1, wherein the adduct III is separated from the adduct II and the adduct III is then recycled to the reaction a) and is isomerized therein to the adduct II.

4. A process as defined in claim 1, wherein the reactions c)—isomerization of the adduct II to the enamine IV—and d)—hydrolysis or combined hydrolysis/hydrogenation of the enamine IV to n-butyraldehyde and n-butanol—are carried out in a single process stage.

5. A process as defined in claim 1, wherein the reactions c) and d) are carried out in the presence of a heterogeneous catalyst containing copper.

6. A process as defined in claim 1, wherein the reaction c) and d) are carried out in the liquid phase in the presence of a homogeneous catalyst soluble in the reaction medium, which catalyst is a mono- or polydentate phosphine or phosphite complex of a Group Ib, VIb, VIIb, and VIIIb element.

7. A process as defined in claim 1, wherein the partial reactions d) is carried out in the presence of an acid ion exchanger.

8. A process for the preparation of 2-ethylhexanol, wherein 1,3-butadiene is caused to react with an amine of the formula I

   I in which $R^1$ and $R^2$ independently denote hydrogen, optionally substituted aliphatic or cycloaliphatic radicals, or aryl or aralkyl radicals or are linked to form a nitrogen-containing bridging member, which bridging member can contain an additional nitrogen atom and/or oxygen atom, the number of bridging atoms being from 3 to 6 at elevated temperature and under superatmospheric pressure in the presence of a compound of a Group VIIIb element to form a mixture of the adducts of the formulas II

   II and III

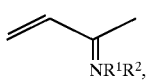   III b) the adduct III is optionally isomerized to the adduct II c) the adduct II is isomerized in the presence of a homogeneous or heterogeneous transition metal element catalyst in the liquid phase to form the enamine of the formula IV

   IV e) n-butyraldehyde is produced from this enamine IV by the reaction thereof with water in the presence of the catalyst used in partial reaction c) and in the presence of an acid, f) the n-butyraldehyde is converted to the aldol product 2-ethylhex-2-enal, g) the said aldol product is hydrogenated to 2-ethylhexanol, amine I being liberated, which amine I is recycled to the stage defined above as reaction a).

* * * * *

UNITED STATES PATENT AND TRADEMARK OFFICE
CERTIFICATE OF CORRECTION

PATENT NO.: 5,892,125

DATED: April 6, 1999

INVENTOR(S): KANAND et al.

It is certified that error appears in the above-identified patent and that said Letters Patent is hereby corrected as shown below:

On the cover page, item [86], both the § 371 and § 102(e) dates should be --Jun. 23, 1997--.

Signed and Sealed this

Nineteenth Day of October, 1999

Attest:

Q. TODD DICKINSON

*Attesting Officer*   *Acting Commissioner of Patents and Trademarks*